(12) United States Patent
Stephens et al.

(10) Patent No.: US 11,896,683 B2
(45) Date of Patent: Feb. 13, 2024

(54) RADIOLABELLED MATERIAL FOR TARGETED ADMINISTRATION

(71) Applicant: The Australian National University, Australian Capital Territory (AU)

(72) Inventors: Ross Wentworth Stephens, Australian Capital Territory (AU); Gregory David Tredwell, Australian Capital Territory (AU); Karen Joanne Knox, Upper Coomera (AU); Lee Andrew Philip, Greenleigh (AU); Rebecca Greenlees, Australian Capital Territory (AU); Keira Beattie, Australian Capital Territory (AU)

(73) Assignee: THE AUSTRALIAN NATIONAL UNIVERSITY, Australian Capital Territory (AU)

( * ) Notice: Subject to any disclaimer, the term of this patent is extended or adjusted under 35 U.S.C. 154(b) by 109 days.

(21) Appl. No.: 16/469,244

(22) PCT Filed: Dec. 15, 2017

(86) PCT No.: PCT/AU2017/000279
§ 371 (c)(1),
(2) Date: Jun. 13, 2019

(87) PCT Pub. No.: WO2018/107205
PCT Pub. Date: Jun. 21, 2018

(65) Prior Publication Data
US 2020/0038528 A1    Feb. 6, 2020

(30) Foreign Application Priority Data

Dec. 16, 2016  (AU) ................ 2016905219

(51) Int. Cl.
*A61K 51/12*   (2006.01)
*A61P 35/00*   (2006.01)
*A61K 51/06*   (2006.01)

(52) U.S. Cl.
CPC ........ *A61K 51/1251* (2013.01); *A61K 51/065* (2013.01); *A61K 51/1282* (2013.01); *A61P 35/00* (2018.01)

(58) Field of Classification Search
CPC ... A61P 35/00; A61K 51/1282; A61K 51/065; A61K 51/1251; A61K 51/088
See application file for complete search history.

(56) References Cited

U.S. PATENT DOCUMENTS 5,364,613 A * 11/1994 Sieving ............... A61K 51/065
                                                424/9.3
6,203,775 B1 * 3/2001 Torchilin ................ C07K 1/13
                                                530/391.5
2003/0120355 A1 6/2003 Hafeli et al.
2004/0258614 A1 12/2004 Ghandehari et al.
2007/0154513 A1* 7/2007 Atanasoska ............ A61L 31/08
                                                424/423
2010/0158813 A1* 6/2010 Paradossi ............... A61K 9/122
                                                424/9.52
2011/0097275 A1 4/2011 Arbogast et al.
2013/0302243 A1 11/2013 Borbely et al.
2016/0151518 A1* 6/2016 Stephens .............. A61K 51/065
                                                424/1.37

FOREIGN PATENT DOCUMENTS

| CN | 101321542   | 12/2008 |
| WO | 1996/010359 | 4/1996  |
| WO | 1996/011712 | 4/1996  |
| WO | 2005/061006 | 7/2005  |
| WO | 2007047668  | 4/2007  |
| WO | 2009129578  | 10/2009 |
| WO | 2011011592  | 1/2011  |
| WO | 2014207490  | 12/2014 |
| WO | 2015/000012 | 1/2015  |
| WO | 2015000012  | 1/2015  |

OTHER PUBLICATIONS

Sano et al., J. Controlled Release, 2014, 194, p. 310-315. (Year: 2014).*
Barrefelt et al., EJNMMI Research, 2013, 3:12. (Year: 2013).*
Extended European Search Report prepared for European Patent Application No. 17879749.4, dated Jun. 29, 2020.
PCT International Search Report prepared for PCT/AU2017/000279, dated Mar. 13, 2018.
Stockhofe, K., Postema, J., Schieferstein, H., & Ross, T. (2014). Radiolabeling of nanoparticles and polymers for PET imaging. Pharmaceuticals, 7(4), 392-418.

* cited by examiner

*Primary Examiner* — Michael G. Hartley
*Assistant Examiner* — Leah H Schlientz
(74) *Attorney, Agent, or Firm* — Brannon Sowers & Cracraft PC

(57) ABSTRACT

The invention relates to a radiolabelled material comprising a polymer, a radioactive isotope, and an immobilizing agent, wherein the immobilizing agent is capable of immobilizing the radioactive isotope on or in the polymer, and wherein the immobilizing agent is a macromolecule comprising a polycation with multiple pendant metal-chelating side-chains. The invention also relates to a process for making a radiolabelled material, to use of a radiolabelled material for the preparation of medicaments for treating cancer and/or for radiation imaging and to use of a radiolabelled material in the treatment of cancer. There is further described use of an immobilizing agent to immobilize a radioactive isotope on or in a polymer.

19 Claims, 17 Drawing Sheets

RADIOLABELLED MATERIAL FOR TARGETED ADMINISTRATION

CROSS-REFERENCE TO RELATED APPLICATION

This application is a U.S. national entry application under 37 C.F.R. § 371(b) of International Application Serial No. PCT/AU2017/000279 filed Jun. 15, 2017, which claims the right of priority and benefit under 35 U.S.C. §§ 119 & 365 of AU Patent Application No. 2016905219 filed on Dec. 16, 2016, the disclosures of which are incorporated herein by reference in their entirety.

TECHNICAL FIELD

The present invention relates to the preparation of radiolabelled materials, such as radiolabelled polymers for use in medical applications. In particular, the present invention relates to the use of radiolabelled materials in regional and targeted radiotherapy, and in radioactive imaging.

BACKGROUND

The local administration of radioactive materials may be used as a treatment for cancer, and in particular for cancers which are difficult to successfully treat by surgery alone. The radioactive materials are incorporated into devices such as microparticles, seeds and wires which are directly implanted into the cancer.

Selective internal radiation therapy (SIRT) is a form of radiation therapy which involves injecting microspheres of radioactive material into the arteries that supply the tumour.

For example, the resin based "SIR-Spheres®" (SIR-Spheres® is a registered trademark of Sirtex SIR-Spheres Pty Ltd) microspheres carry the $^{90}Y$ isotope and are used for SIRT. SIR-Spheres® have found particular application in the treatment of liver cancer. $^{90}Y$ is very suitable for beta radiation therapy as tumor cells are killed within a radius of 1 to 2 mm. However, beta radiation is very poor for imaging. Bremsstrahlung imaging (which uses a photon produced by the deceleration and subsequent loss of kinetic energy when the particles produced during beta decay are deflected by other charged particles in the tissue) is not very accurate as it is not a true representation of where the isotope actually is and gives poor resolution images. Therefore, it can be difficult to ascertain whether the radiation has been successfully delivered to the target organ and to what extent.

SIR-Spheres® have found particular application in the treatment of liver cancer. There remains a need for the targeted administration of radioisotopes to other target organs for both therapeutic and imaging applications.

Lung cancer is one of the most aggressive of all cancers, having a 5 year survival rate of only approximately 10%. Surgery is uncommon in lung cancer patients and despite a number of chemotherapeutics being available there remains a need for improved therapies for lung cancer. Several other cancer types metastasize to the lungs, providing a further reason for a need for improved treatments for lung cancer. SIR-Spheres® are not, however, particularly suitable for the treatment of lung cancer due to the lack of imaging properties, as discussed above. In addition, $^{90}Y$ is a very high energy isotope that is not as suitable for the lungs as it is for the liver. The lungs are more sensitive to radiation than the liver which has some capacity for regeneration after injury.

In WO 2009/129577 it was shown that administration of poly-D-lysine (PDL) coated Tc-99m nanoparticles (Fibrin-Lite) was an effective way to produce specific accumulation of a radiolabel in the blood vessel network of the lungs, thus enabling imaging of said network. Poly-D-lysine treated Tc-99m FibrinLite is an example of a targeted imaging agent for lung diagnostics/prognostics. These poly-D-lysine coated Tc-99m nanoparticles are, however, not suitable for therapeutic applications as Tc-99m is only suitable for gamma imaging techniques. In addition, PDL coated Fibrin-Lite nanoparticles are only retained in the lungs for a half-life of approximately 3 hours. While a 3 hour half-life is adequate for an imaging agent, for therapeutic applications it is necessary for the radiolabelled material to be retained in the lung for a longer time period to provide a therapeutic dose of radiation.

There remains a need for alternative radiolabels and a means to retain the radiolabel in the lung longer in order for a therapeutic dose of beta radiation to be delivered. Moreover the particles used must not produce embolism or occlusion impacting on respiration.

Existing treatments also present the following problems.

The radioactive elements often have short half-lives, and the time elapsed between the manufacture of the radioactive material and the administration to the patient may result in significant loss of activity. This in turn leads to high costs associated with manufacture and transportation of the radioactive materials to the hospital and patient.

Incomplete retention of the radionuclide on the device can result in leaching of the radionuclide and unintended dissemination to non-target organs. It is therefore desirable to have the maximum control over the dosing of the radiation as possible, in order to deliver the radiation to the target organ in preference to healthy tissues.

The radioactive material can often only accommodate one particular radioactive element, rather than two or more radioactive elements, which can restrict the versatility of the treatment program.

It is therefore an object of the invention to provide a radiolabelled material for the treatment of cancer, in particular lung cancer, which overcomes one or more of the above problems. In particular, it is desirable to develop a method by which the subsequent organ distribution of therapeutic microspheres may be more accurately predicted. Further, if therapeutic microspheres are administered, it is desirable to have a reliable method for determining the precise site of radiation exposure in the patient's body in order to determine the effectiveness of the treatment and the necessity for future treatments.

SUMMARY OF INVENTION

In a first aspect of the invention, there is provided a radiolabelled material comprising:
 (i) a polymer;
 (ii) a radioactive isotope; and
 (iii) an immobilizing agent;
wherein the polymer is a cationic exchange resin comprising anionic substituent groups; and
wherein the immobilizing agent is capable of immobilizing the radioactive isotope on or in the polymer, and wherein the immobilizing agent is a macromolecule comprising a polycation with multiple pendant metal-chelating agent sidechains.

In a second aspect of the invention, there is provided a dual radiolabelled material comprising:
 (i) a polymer;
 (ii) a first radioactive isotope;
 (iii) a second radioactive isotope;

(iv) a first immobilizing agent; and
(v) a second immobilizing agent;
wherein the polymer is a cationic exchange resin comprising anionic substituent groups; and
wherein the first immobilizing agent is capable of immobilizing the first radioactive isotope on or in the polymer, and wherein the first immobilizing agent is a macromolecule comprising a polycation with multiple pendant metal-chelating agent side-chains; and wherein the second immobilizing agent is capable of immobilizing the second radioactive isotope on or in the polymer, and wherein the second immobilizing agent is a macromolecule comprising a polycation with multiple pendant metal-chelating agent side-chains.

In a third aspect of the invention, there is provided a dual radiolabelled material comprising:
(i) a polymer;
(ii) a first radioactive isotope;
(iii) a second radioactive isotope; and
(iv) an immobilizing agent;
wherein the polymer is a cationic exchange resin comprising anionic substituent groups; and
wherein the immobilizing agent is capable of immobilizing the first radioactive isotope and the second radioactive isotope on or in the polymer and wherein the immobilizing agent is a macromolecule comprising a polycation with multiple pendant metal-chelating agent side-chains.

In a fourth aspect of the invention, there is provided a process for making a radiolabelled material according to the first aspect above comprising:
(i) mixing the polymer according to the first aspect above with an immobilizing agent according to the first aspect above;
(ii) optionally washing the resulting mixture;
(iii) further adding a radioactive isotope according to the first aspect; and
(iv) optionally washing the resulting mixture.

The above order of the steps in the process is not limiting; the order of the steps may also be:
(i) mixing the polymer according to the first aspect above with a radioactive isotope according to the first aspect above;
(ii) optionally washing the resulting mixture;
(iii) further adding an immobilizing agent according to the first aspect; and
(iv) optionally washing the resulting mixture.

In a fifth aspect of the invention, there is provided use of an immobilizing agent to immobilize a radioactive isotope on or in a polymer, wherein the immobilizing agent, the radioactive isotope and the polymer are according to the first aspect of the invention.

In a sixth aspect of the invention, there is provided use of the radiolabelled material according to the first aspect of the invention, or the dual radiolabelled material of the second or third aspect of the invention, for the manufacture of a medicament for the treatment of cancer and/or for radiation imaging.

In a seventh aspect the invention provides a method of radiation therapy of a patient, the method comprising administering to said patient a therapeutically effective amount of the radiolabelled material of the first aspect of the invention, or the dual radiolabelled material of the second or third aspect of the invention.

In one embodiment the radiation therapy is internal radiation therapy for the lung. For example, the radiation therapy is for the treatment of primary and/or metastatic lung tumours.

In a sixth aspect of the invention, there is provided a method for the treatment of cancer, the method comprising administering a therapeutically effective amount of the radiolabelled material according to the first aspect of the invention, or the dual radiolabelled material of the second or third aspect of the invention, to a patient in need thereof.

In an embodiment, the cancer is a primary sarcoma, a primary or secondary melanoma, a primary head and neck cancer, a primary or secondary brain cancer, a primary or secondary lung cancer, a primary or secondary liver cancer, a primary or secondary breast cancer, a primary or secondary kidney cancer (renal carcinoma), a primary or secondary ovarian cancer, a primary or secondary prostate cancer or a neuroendocrine cancer.

In one embodiment the cancer is primary or secondary lung cancer.

In a seventh aspect of the invention, there is provided a medical device comprising the radiolabelled material according to the first aspect of the invention, or the dual radiolabelled material of the second or third aspect of the invention.

In one embodiment the medical device is a microsphere, seed, stent, catheter, wire or wafer.

In an eighth aspect the invention provides a method of imaging a medical procedure in a patient, the method comprising administering to said patient the radiolabelled material according to the first aspect of the invention, or the dual radiolabelled material of the second or third aspect of the invention, and detecting said radiolabelled material or said dual radiolabelled material in said subject.

In one embodiment the detecting comprises gamma camera imaging of said radioactivity.

BRIEF DESCRIPTION OF DRAWINGS

FIG. 4B shows the gamma camera image of the lung and heart following removal of the heart from the lung.

FIG. 12 shows lung tissue from mice stained with hematoxylin and eosin at 40× magnification. Some of the microspheres are highlighted with arrows and the white bars show 50 microns (µm).

FIG. 13 shows lung tissue from mice stained with hematoxylin and eosin at 40× magnification. Some of the microspheres are highlighted with arrows.

FIG. 13 shows lung tissue from rabbits stained with hematoxylin and eosin at 40× magnification. A single rabbit had small granulomas randomly dispersed throughout the pulmonary parenchyma (left), which was not present in any of the other rabbit samples. Some of the microspheres are highlighted with arrows.

ABBREVIATIONS AND DEFINITIONS

Figure 1:
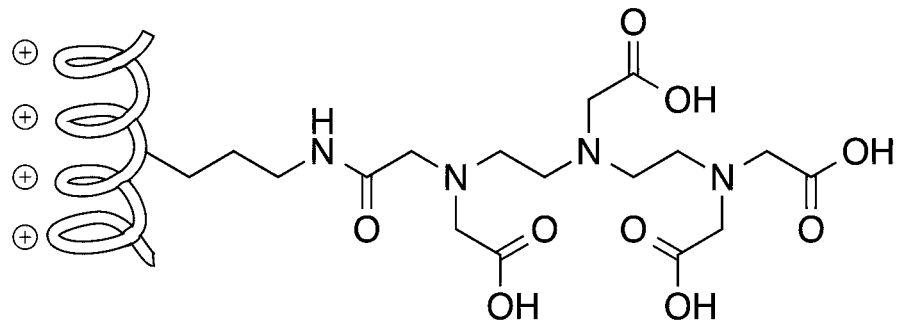
FIG. 1 shows a representation of a polymeric immobilizing agent, based on DTPA covalently linked to poly-L-omithine (PLO). The PLO backbone is represented by the coil on the left with pendant substituents of DTPA linked through an amide linkage. Amino groups of PLO that have not been substituted are free to accept protons and form a positive charge as indicated.

For convenience, the following abbreviations used in this specification are listed below.

As used herein the term "SPECT" is an abbreviation for single photon emission computed tomography.

As used herein the term "PET" is an abbreviation for positron emission tomography.

As used herein the term "CT" is an abbreviation for computed tomography.

As used herein the term "MRI" is an abbreviation for magnetic resonance imaging.

As used herein the term "SIRT" is an abbreviation for selective internal radiation therapy.

As used herein the term "PDL" is an abbreviation for poly-D-lysine.

As used herein the term "PLO" is an abbreviation for poly-L-ornithine.

As used herein the term "EDTA" is an abbreviation for ethylenediaminetetraacetic acid.

As used herein the term "DOTA" is an abbreviation for 1,4,7,10-tetraazacyclododecane-1,4,7,10-N,N',N'',N'''-tetraacetic acid.

As used herein the term "DTPA" is an abbreviation for diethylenetriaminepentaacetic acid.

As used herein the term metal "chelating agent" or "chelator" refers to a polydentate ligand that forms two or more separate coordinate bonds with a single central atom, in particular with a radioactive isotope.

The term "therapeutically effective amount" as used herein includes within its meaning a non-toxic but sufficient amount of a compound or composition for use in the invention to provide the desired therapeutic effect. The exact amount required will vary from subject to subject depending on factors such as the species being treated, the age, weight and general condition of the subject, co-morbidities, the severity of the condition being treated, the particular agent being administered and the mode of administration and so forth. Thus, for any given case, an appropriate "effective amount" may be determined by one of ordinary skill in the art using only routine methods.

In the context of this specification, the term "comprising" means "including principally, but not necessarily solely". Furthermore, variations of the word "comprising", such as "comprise" and "comprises", have correspondingly varied meanings. Hence, the term "comprising" and variations thereof is used in an inclusive rather than exclusive meaning such that additional integers or features may optionally be present in a composition, method, etc. that is described as comprising integer A, or comprising integer A and B, etc.

In the context of this specification the term "about" will be understood as indicating the usual tolerances that a skilled addressee would associate with the given value.

In the context of this specification, where a range is stated for a parameter it will be understood that the parameter includes all values within the stated range, inclusive of the stated endpoints of the range. For example, a range of "5 to 10" will be understood to include the values 5, 6, 7, 8, 9, and 10 as well as any sub-range within the stated range, such as to include the sub-range of 6 to 10, 7 to 10, 6 to 9, 7 to 9, etc, and inclusive of any value and range between the integers which is reasonable in the context of the range stated, such as 5.5, 6.5, 7.5, 5.5 to 8.5 and 6.5 to 9, etc.

In the context of this specification, the term "plurality" means any number greater than one.

To the extent that it is permitted, all references cited herein are incorporated by reference in their entirety.

It is to be noted that reference herein to use in medicine will be understood to be equally applicable to human and non-human, such as veterinary, applications. Hence it will be understood that, except where otherwise indicated, reference to a patient, subject or individual means a human or non-human, such as an individual of any species of social, economic or research importance including but not limited to lagomorph, ovine, bovine, equine, porcine, feline, canine, primate and rodent species.

Similarly, it is to be noted that reference herein to a "medical" device will be understood to be equally applicable to a medical device suitable for use in human and non-human, such as veterinary, applications.

As used herein the term "device" will be understood to include devices which may be used in therapy, including preventative and treatment of an actual condition or symptom, and those which may be used in diagnosis, including where the diagnosis is performed on or in the body of a patient and where the diagnosis is performed on or with a sample obtained from the body of a patient. Accordingly, the term "device" as used wherein includes therapeutic devices and diagnostic devices.

As used herein "diagnosis" will be understood to include investigative procedures performed in circumstances where a disease or condition is suspected, such as for initial investigation, prognosis, progression of a disease or condition whether in the presence or the absence of therapy, and in circumstances where no such suspicion exists but where investigation is desired, such as for the purposes of health checks, population screening or research.

DETAILED DESCRIPTION

The present invention provides a radiolabelled material comprising:
(i) a polymer;
(ii) a radioactive isotope; and
(iii) an immobilizing agent;

wherein the polymer is a cationic exchange resin comprising anionic substituent groups; and
wherein the immobilizing agent is capable of immobilizing the radioactive isotope on or in the polymer, and wherein the immobilizing agent is a macromolecule comprising a polycation with multiple pendant metal-chelating agent side-chains.

Imnmobilizing Agent

The immobilizing agent is a compound which is capable of immobilizing the radioactive isotope on or within the polymer. In one embodiment the immobilizing agent is a macromolecule comprising a polycation with multiple pendant metal-chelating agent side chains.

In one embodiment the macromolecule is a tissue-specific, organ-specific, cell type-specific, or disease state-specific macromolecule. In one embodiment the macromolecule is specific for lung. In one embodiment the macromolecule binds to the heparan sulfate proteoglycans (HSPGs) in the lungs. In one embodiment the macromolecule is a polycation. In one embodiment the polycation is selected from poly-D-lysine (PDL) and poly-L-ornithine (PLO). In one embodiment the polycation is PDL. In one embodiment the PDL is of molecular weight about 4 kD to about 15 kD. In another embodiment the polycation is PLO. In one embodiment the PLO is of molecular weight of about 5 kD to about 15 kD.

The immobilizing agent is preferably a polycationic macromolecule which comprises a polypeptide backbone made up of PDL or PLO, to confer the advantage of being non-biodegradable by endogenous proteinases. Preferably, the polycationic macromolecule has a polypeptide backbone with pendant side chains covalently attached at intervals along its length, such that there are pendant side chains spaced 2 to 6 amino acid residues apart and unsubstituted positively-charged amino acid side chains in between. In one embodiment the polycation retains enough positively-charged amino acid side chains along the polypeptide backbone so as not to affect the binding affinity of the polycation for the HSPGs in the lung.

Preferably, the covalently attached pendant side chains comprise metal-chelators.

In an embodiment, the immobilizing agent is a polycation with multiple covalently linked side chains of a metal-chelating agent. In an embodiment, the immobilizing agent is a polyamino acid with multiple covalently linked side chains of a metal-chelating agent. In an embodiment, the immobilizing agent is selected from PDL or PLO with multiple covalently linked side chains of a metal-chelating agent.

In an embodiment, the metal-chelating agent is selected from the group consisting of ethylenediaminetetraacetic acid (EDTA), 1,4,7,10-tetraazacyclododecane-1,4,7,10-N,N',N", N'''-tetraacetic acid (DOTA), diethylenetriaminepentaacetic acid (DTPA), mercaptoacetyltriglycine ($MAG_3$), 6-Hydrazinopridine-3-carboxylic acid (Hynic), dimercaptosuccinic acid (DMSA), ethylene glycol-bis(β-aminoethyl ether)-N,N,N',N'-tetraacetic acid (EGTA), triethylenetetramine (TETA), 1,4,7,10-tetraazacyclotridecane-1,4,7,10-N,N',N",N'''-tetraacetic acid (TRITA), 1,4,7-triazacyclononane-1,4,7-triacetic acid (NOTA), deferoxamine (desferral), sarcophagine (SarAr), 1,4,7,10-tetraazacyclododecane-1,4,7,10-N,N',N",N'''-tetra(methylene) phosphonic acid (DOTMP); 1,4,7,10-tetraazacyclotridecane-1,4,7,10-N,N',N",N'''-tetra(methylene)phosphonic acid; 1,4,7,10-tetraazacyclotetradecane-1,4,7,10-N,N',N",N'''-tetra(methylene) phosphonic acid; diethylene triamine-N,N',N"-pentaacetic acid and isomeric derivatives thereof; cryptate [2,2,2], cryptate[3,2,2], cryptate[2,2,1] and mono and di-benzo derivatives thereof; bridged calix[4]arenes containing electron rich (donor) groups (hydroxyl, carboxyl, ester, amid, amine); 1,10-diaza-4,7,13,16-tetraoxacyclooctadecane-1,10-N,N'-bis-acetic acid; and 1,10-diaza-4,7,13, 16 tetraoxacyclooctadecane-1,10-N,N'-bis-malonate; and derivatives of any of these metal chelating agents, and any other multidentate or macrocyclic metal chelating agents known to those skilled in the art.

Preferably the metal-chelating agents are selected to maintain immobilisation of the selected radioactive isotopes under in vivo conditions.

A person skilled in the art will appreciate that the choice of metal-chelating agent will depend upon the radioactive isotope to be chelated. A metal-chelate that is suitable for one radioactive isotope will not necessarily be the best metal-chelate for another radioactive isotope.

PDL or PLO with pendant covalently linked side chains of DTPA or DOTA is a preferred immobilizing agent of the present invention, as they are non-biodegradable by endogenous proteases.

In one embodiment the pendant metal-chelating agent is DTPA and the polycation is PLO. In another embodiment the pendant metal-chelating agent is DOTA and the polycation is PLO. In a further embodiment the pendant metal-chelating agent is DTPA and the polycation is PDL. In another embodiment the pendant metal-chelating agent is DOTA and the polycation is PDL.

In an embodiment there is one pendant chelator molecule at every 2 to 6 amino acid residues in the polycation chain. In one embodiment there is one pendant chelator molecule at every 2, 3, 4, 5 or 6 amino acid residues in the polycation chain. In one embodiment there is one pendant chelator molecule at every 2 to 5 amino acid residues in the polycation chain. In another embodiment there is one pendant chelator molecule at every 2 to 4 amino acid residues in the polycation chain.

In one embodiment the molar ratio of the pendant metal-chelating agents to the polycation is between about 7 and 20. In another embodiment the molar ratio of the pendant metal-chelating agents to the polycation is between about 12 and 18. In a further embodiment the molar ratio of the pendant metal-chelating agents to the polycation is between about 13 and 17.

In one embodiment the pendant metal-chelating agent is DTPA and the polycation is PLO. In one embodiment the molar ratio of DTPA to PLO is between about 7 and 20. In another embodiment the molar ratio of DTPA to PLO is between about 12 and 18. In a further embodiment the molar ratio of DTPA to PLO is between about 13 and 17.

Polymer

The polymer of the present invention may be any polymer having a surface that is biocompatible with blood (i.e. does not promote blood coagulation by the so-called intrinsic pathway, or thrombosis by promotion of platelet adhesion).

In one embodiment the polymer of the present invention is a cationic exchange resin comprising anionic substituent groups, such as sulfate, sulfonate, carboxylate and phosphate groups in order to bind the polycation.

For example, the polymer may be any blood biocompatible polymer known in the art, including but not limited to polystyrene, polystyrene sulfonate, polypropylene, polytetrafluoroethylene (PTFE), expanded polytetrafluoroethylene (EPTFE), polyurethane, polyvinyl chloride, polyamides, teflon, polyester, polyethylene terephthalate, poly(butylene terephthalate) (PBT), poly(ethylene oxide) (PEO), polylactide (PLA), polyglycolide (PGA), poly(lactide-co-glycolide) (PLGA), poly(e-caprolactone), polydioxanone, trimethylene carbonate, polyanhydride, and poly[bis(p-carboxyphenoxy) propane:sebacic acid. Preferably, the polymer is polystyrene sulfonate.

In particular, polytetrafluorethylene (PTFE), expanded polytetraflouroethylene (EPTFE), polyurethane, polyvinyl chloride, polyamides, polystyrene and teflon may be employed as polymers in the present invention.

Polymers which may be used for vascular grafts include polyester, for example polyethylene terephthalate, polyurethane, and polytetrafluoroethylene.

The polymer may be adhered to or in the form of a catheter, a fibre, rod or filament, wire, membrane, wafer, mesh, gauze, porous sponge, tube, stent, bead, capsule, microparticles, microspheres, nanoparticles and liposomes. Preferably, the polymer is in the form of microspheres, seeds, a stent, catheter, wire or a wafer. Stents may be used with radioisotopes for endovascular brachytherapy to prevent reocclusion during the short post-operative period, in which the stent includes a radioisotope to inhibit proliferation of smooth muscle cells.

The polymer microspheres are appropriately sized to provide retention at the pre-capillary level of the lung's arterial network. The microspheres preferably have a median diameter of between 0.5 and 200 microns, of between 0.5 to 50 microns, up to 35 microns or between 0.5 and 35 microns. Examples of radionuclide-containing microspheres are described in U.S. application Ser. No. 11/192,299.

In an embodiment, the polymer is in the form of particulate microspheres having a median diameter of between 0.5 and 100 microns. In an embodiment, the particulate microspheres have a median diameter of 0.5 to 50 microns. In an embodiment, the particulate microspheres have a median diameter of up to 35 microns. In an embodiment, the particulate microspheres have a median diameter of 0.5 to 35 microns. In one embodiment the particulate microspheres have a median diameter of 8 to 12 microns. In another embodiment the particulate microspheres have a median diameter of 8 microns. In a further embodiment the particulate microspheres have a median diameter of 1 micron. In a still further embodiment the particulate microspheres have a median diameter of 30 microns.

The polymer microspheres for use in the present invention includes those used in the manufacture of SIR-Spheres® (SIR-Spheres® is a registered trademark of Sirtex SIR-Spheres Pty Ltd) microspheres, which are resin based microspheres comprised of polystyrene sulfonate.

Radioactive Isotope

The radioactive isotope of the present invention enables imaging and/or therapy. Preferably, the imaging includes SPECT imaging, and/or PET imaging.

Single-photon emission computed tomography (SPECT) is a nuclear medicine tomographic imaging technique using gamma rays and is able to provide true 3D information. The information is often presented as cross-sectional slices through the patient. Due to the gamma-emission of the isotope, it is possible to see where the radiolabelled material has accumulated in the patient's body. Such a true 3D representation can be helpful in tumour imaging.

Positron emission tomography (PET) is a nuclear medicine imaging technique that produces a 3D image and has a higher sensitivity than traditional SPECT imaging. The system detects pairs of gamma rays emitted indirectly by a positron-emitting radionuclide (tracer), which is introduced into the body. 3D images of tracer concentration within the body are then constructed by computer analysis and the 3D imaging is often accomplished with the aid of a computed tomography (CT) X-ray scan performed on the patient during the same session, in the same machine. Positron-emitting isotopes can also be used in conjunction with CT to provide 3D imaging of the anatomical distribution of a labelled medical device.

In an embodiment, the radioactive isotope enables imaging and/or therapy. In an embodiment, the imaging includes SPECT imaging, and/or PET imaging. In an embodiment, the radioactive isotope is selected from Ac-225, Au-198, Bi-212, Bi-213, Co-57, Cr-51, Cu-64, Cu-67, Dy-165, Er-169, Fe-59, Ga-67, Ga-68, Gd-153, Ho-166, In-111, Ir-192, Lu-177, Pd-103, Rb-81, Rb-86, Re-186, Re-188, Ru-103, Sc-47, Sm-153, Sn-117m, Sr-89, Tb-161, Tc-99m, Tl-201, Y-90, Yb-169 and Zr-89. In an embodiment, the radioactive isotope is selected from Group XIII of the periodic table. In an embodiment, the radioactive isotope is Ga-67, In-111, Lu-177, Tl-201 or Y-90.

The radioactive isotopes of the present invention may include radioactive metal or semi-metal isotopes. Preferably, the radioactive isotopes are water soluble metal cations.

Examples of suitable radioactive metal isotopes of the present invention include Ac-225, Au-198, Bi-212, Bi-213, Co-57, Cr-51, Cu-64, Cu-67, Dy-165, Er-169, Fe-59, Ga-67, Ga-68, Gd-153, Ho-166, In-111, Ir-192, Lu-177, Pd-103, Rb-81, Rb-86, Re-186, Re-188, Ru-103, Sc-47, Sm-153, Sn-117m, Sr-89, Tb-161, Tc-99m, Tl-201, Y-90, Yb-169 and Zr-89.

In particular, the radioactive isotope of the present invention includes those elements in the group XIII (the Boron Family) of the periodic table, which includes Ga and In.

In particular, preferred radioactive isotopes include Ga-67, Ga-68, Lu-177, Y-90, and In-111. Most preferably, radioactive isotopes are Lu-177 and Y-90. In one embodiment the radioactive isotope is Lu-177.

The radioactive isotope of the present invention also includes transition metals, such as Lu-177, Y-90, Cu-64, Cu-67 and Tb-161. Preferably, the radioactive isotope is Lu-177 or Y-90.

The isotopes of the present invention are understood to also include the parent isotopes.

The radiolabelled material of the present invention may comprise a combination of at least two radioactive isotopes to enable imaging and/or therapy. The combination of radioactive isotopes may be selected from Ga-68 and Lu-177; Ga-67 and Y-90; Ga-68 and Y-90; In-111 and Y-90; Lu-177 and Y-90, and Ga-67 and Tb-161.

The present invention may further include the use of at least one non-radioactive, non-toxic carrier metals. For example, the carrier metal may be selected from Bi and Fe.

In particular, the non-radioactive carrier metal enables MRI imaging (for example Fe) or X-ray contrast imaging (for example Bi).

Further examples of carrier metals include the trivalent bismuth, which additionally provides X-ray contrast in the microspheres, so that they can be imaged in CT.

The radiolabelled material according to the present invention may emit alpha, beta, gamma and/or positron radiation.

Radiolabelled Material

The radiolabelled material of the present invention comprises a polymer, a radioactive isotope and an immobilizing agent, wherein the immobilizing agent is capable of immobilizing the radioactive isotope on or in the polymer and wherein the immobilizing agent is a macromolecule comprising a polycation with multiple pendant metal-chelating agent side-chains.

In one embodiment of the present invention the radiolabelled material makes use of the polycation of the immobilizing agent as an ion pair to anchor the covalently linked multiple pendant metal-chelating agents to the surface of a polymer. In one embodiment the polymer is an anionic polystyrene sulfonate microsphere and the polycation of the immobilizing agent forms an ion pair with the anionic sulfonated surface of the polymer microsphere. The chelate substitution of the polycation side-chains of the immobilizing agent is kept to a minimum so as to preserve enough polycationic character for the ion pair attachment to the sulfonated surface of the polymer. The polycation:sulfonate multisite interaction then serves as a strong "zipper" to hold the composite together, with the radioisotope bound to the pendant chelates. By this means the inventors have found that it is possible to secularly load enough radioisotope activity to achieve a radiation dose in the therapeutic range, which is stably retained on the polymer under in vivo conditions.

The immobilizing agent of the present invention is able to immobilize one or more radioactive elements on the polymer, each producing different levels and types of radiation (such as gamma and beta radiation) and having different half-lives. Therefore, the radiolabelled material of the invention may comprise a radioactive isotope to enable imaging (such as by SPECT or PET) and/or a radioactive isotope to enable therapy. Therefore, the same polymer particles may be employed in the investigative imaging procedure (i.e. as "mimic" particles) and the therapeutic procedure. In this way, the mimic particles can accurately predict the organ distribution of the therapeutic particles to give an accurate estimate of the number of patients deemed suitable for therapeutic particles.

In one embodiment the radiolabelled material of the present invention is a dual radiolabelled material comprising a polymer, a first radioactive isotope, a second radioactive isotope and an immobilizing agent, wherein the immobilizing agent is capable of immobilizing the first radioactive isotope and the second radioactive isotope on or in the polymer and wherein the immobilizing agent is a macromolecule comprising a polycation with multiple pendant metal-chelating agent side-chains. In one embodiment the immobilizing agent comprises a polycation with multiple pendant first metal-chelating side-chains and multiple pendant second metal-chelating side chains. In one embodiment the first metal-chelating side chain immobilizes the first radioactive isotope and the second metal-chelating side chain immobilizes the second radioactive isotope. In one embodiment the first radioactive isotope enables imaging and the second radioactive isotope enables therapy.

In one embodiment the dual radiolabelled material of the present invention comprises a polymer, a first radioactive isotope, a second radioactive isotope, a first immobilizing agent and a second immobilizing agent, wherein the first immobilizing agent is capable of immobilizing the first radioactive isotope on or in the polymer and the second immobilizing agent is capable of immobilizing the second radioactive isotope on or in the polymer and wherein the first immobilizing agent and the second immobilizing agents are each macromolecules comprising a polycation with multiple pendant metal-chelating agent side-chains. In one embodiment the first immobilizing agent is DPTA-PLO and the second immobilizing agent is DOTA-PLO.

Further, the immobilizing agent of the present invention is able to simultaneously immobilize one or more radioisotopes suitable for imaging and therapy on the polymer. Imaging techniques can be employed which can determine the precise site of the therapeutic radiation exposure in the patient's body and therefore enables the determination of the effectiveness of the treatment and the necessity for future treatments.

The immobilizing agent substantially reduces the leaching of the radioactive isotope from the polymer. Therefore, sufficient specific activity (radioactivity per unit mass) can be obtained on the polymer microspheres for imaging and therapy, such that the number of microspheres can be minimized. This avoids using an excessive number of microspheres to achieve an imaging or therapeutic dose, which could otherwise occlude too many blood vessels and thus impair blood perfusion of the organ, and also degrade imaging resolution and therapeutic efficacy by producing local accumulations or clumps of microspheres in vessels. Further, the reduction in leaching of the therapeutic isotope from the microspheres reduces unintended tissue damage in non-target organs.

For example, the immobilizing agent of the present invention is able to bind the important and clinically useful radioactive isotope Lu-177. Lu-177 has both beta and gamma emission, making it suitable for both therapy of some tumours as well as imaging. Lu-177 exhibits a half-life of 6 days. This relatively long half-life is advantageous as there is more time available between manufacture of the radiolabelled material and the administration to the patient before there is significant loss of activity in the radioactive element, therefore leading to lower associated costs. Lu-177 has short range tissue cytotoxicity of only 0.2 mm. Lu-177 is thus a preferred example of a suitable isotope offering both imaging and therapeutic capability.

In a further example, the immobilizing agent of the present invention is able to bind the important and clinically useful isotopes of Gallium, Ga-67 (for SPECT imaging) and Ga-68 (for PET imaging) to the polymer. Ga-67 produces gamma radiation as it decays. Therefore, the position of the radiation can be confirmed using a SPECT or scintigraphic image made from the photon emission, which uses a gamma camera to detect the gamma radiation from the radioactive isotope. Ga-68 produces positron emission as it decays. Positron emission tomography (PET) is a more recent nuclear medicine imaging method that provides superior imaging resolution to SPECT and is also gradually becoming more commonly used. Ga-67 exhibits a half-life of 3.26 days and thus confers further advantage in maintaining sufficient activity during transport and distribution.

In one embodiment, the immobilizing agent is able to bind an optimal imaging isotope (such as for SPECT and/or PET) and an optimal therapeutic isotope (such as a soft or hard beta radiation source) in the one material. Preferably, the immobilizing agent is able to bind at least two isotopes having comparable half-lives. This is advantageous because both the imaging properties and the therapeutic property of the radiolabelled material are then similarly preserved over the time period required for transport and distribution to the point of use. For example, In-11 has a half-life of 2.8 days that is comparable with the half-life of the therapeutic isotope Y-90 (2.67 days).

Preferred combinations of the present invention include Ga-67 or In-11 (SPECT imaging) and Lu-177 (SPECT imaging and beta therapy); Ga-67 or In-111 (SPECT imaging) and Y-90 (beta therapy); and Ga-68 (PET imaging) and Y-90 (beta therapy). A most preferred example is Ga-67 and Y-90.

The ability to immobilize different radioactive isotopes also achieves a more versatile cancer treatment program. The immobilizing agent can be tailored to suit the radioactive isotope to be immobilized and the isotope or isotope combinations can conveniently be chosen to suit the type of cancer and the site of the tumour in the body.

The immobilizing agent functions at acid pH, so the radioactive isotope is not displaced from the polymer anionic groups. In addition, the immobilizing agent enables the radioactive isotope to be retained on the polymer over a pH range 4 to 7 and in vivo after exposure to blood.

Synthesis of Immobilizing Agent

Immobilizing agents of the present invention can be readily prepared by those skilled in the art using methods and materials known in the art and reference to standard textbooks, such as, "Advanced Organic Chemistry" by Jerry March (third edition, 1985, John Wiley and Sons) or "Comprehensive Organic Transformations" by Richard C. Larock (1989, VCH Publishers).

For example, the immobilizing agent can be prepared through standard amide formation by reaction between an amino group on the polycation macromolecule and a carboxylic acid on the metal chelating agent. In one embodiment coupling agents may be employed to activate the carboxylic acid to promote coupling between a primary amine and a carboxylic acid to form an amide bond. In one embodiment the coupling agent is dicyclohexylcarbodiimide (DCC) or 1-ethyl-3-(3-dimethylaminopropyl)carbodiimide (EDC). Preferably the coupling agent is EDC as EDC is a water-soluble carbodiimide.

In a further embodiment an activating agent may be employed in addition to the coupling agent to promote amide bond formation. In one embodiment the activating agent is selected from the group consisting of N-hydroxysuccinimide (NHS), sulfo-N-hydroxysuccinimide (sulfo-NHS), hydroxybenzotriazole (HOBt), 1-hydroxy-7-azabenzotriazole (HOAt) and pentafluorophenol. In one embodiment the activating agent is the water soluble sulfo-NHS. Alternative conditions to catalyse the amide bond formation can be found in the literature, for example in G. T. Hermanson, Bioconjugate Techniques, Academic Press, 2013.

In one embodiment the immobilizing agent is prepared by reaction of a polycation, such as PLO or PDL, and a metal chelating agent, such as DTPA, DOTA or EDTA, in the presence of EDC and sulfo-NHS.

Shown in Scheme 1 is a representative synthesis of an immobilizing agent prepared by reaction of PLO with DTPA using EDC and sulfo-NHS to catalyse the reaction. In Scheme 1, m+n represents the number of ornithine residues in the PLO polycation. For example, 5 kD polyornithine has 43-44 ornithine residues, so m+n=43-44. In the immobilizing agent product, m represents the number of unsubstituted amino group side chains and n represents the number of metal-chelating agents on the polycation backbone of the immobilizing agent.

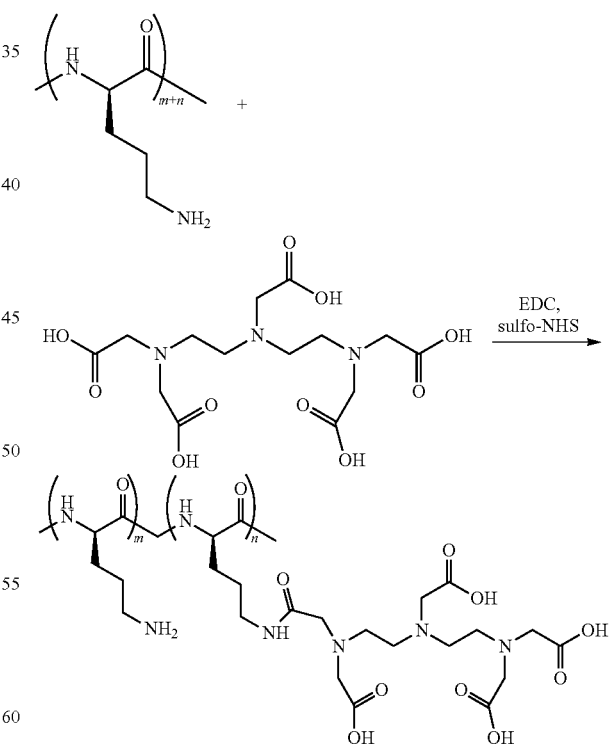

Scheme 1

A person skilled in the art will appreciate that by varying the quantities of various reagents, the number of metal chelating agents incorporated onto the polycation backbone can be varied. For example, by altering the concentration of the linking reagent (EDC) while keeping all other reaction conditions constant different PLO-DTPA constructs can be prepared with different molar ratios of the metal chelating agent to the polycation. The number of metal chelating agents on each polycation chain is calculated as an average value and no separation of the reaction products is conducted. Furthermore, a person skilled in the art would appreciate that the immobilizing agent as depicted in Scheme 1 is representative only—the metal-chelating agent side chains would be distributed along the length of the polyornithine backbone.

The number of metal chelating agents incorporated into the immobilizing agent can be calculated using standard methods known to those skilled in the art. In one embodiment complexometric binding assays can be employed to calculate the number of metal chelating agents in the immobilizing agent.

In one embodiment there is one metal chelating agent for every 2 to 6 amino group side chains. In other words, the molar ratio of the metal chelating agent to the polycation is between about 7 and about 20. The chelate substitution of the polycation side-chains is kept to a minimum so as to preserve enough polycationic character for the ion pair attachment to the sulfonated surface of the polymer.

Those skilled in the art will recognize that alternative immobilizing agents can be prepared by choosing alternative polycations and metal chelating agents. Those skilled in the art will also recognize that immobilizing agents can be prepared with two different pendant metal chelating agents. For example, the polycation could be reacted with two different metal chelating agents to produce an immobilizing agent with two different metal chelating agents, each optimized for immobilizing two different radioactive isotopes. For example an immobilizing agent could be prepared that comprises a polycation with multiple pendant first metal-chelating side-chains and multiple pendant second metal-chelating side chains.

In one embodiment the immobilizing agent can be covalently labelled with other reporter molecules. For example, a fluorescent tag, such as fluorescein can be conjugated to the immobilizing agent. In one embodiment the fluorescently labelled immobilizing agent can be used to quantify the binding of the immobilizing agent to the polymer.

Process to Prepare Radiolabelled Material

The present invention also provides a process for making a radiolabelled material as described above comprising:
(i) mixing the polymer as described above in the section entitled 'Polymer' with an immobilizing agent as described above in the section entitled 'Immobilizing Agent';
(ii) optionally washing the resulting mixture;
(iii) further adding a radioactive isotope as described above in the section entitled 'Radioactive Isotope'; and
(iv) optionally washing the resulting mixture.

Alternatively, the order of the steps can be:
(i) mixing the polymer as described above in the section entitled 'Polymer' with a radioactive isotope as described above in the section entitled 'Radioactive Isotope';
(ii) optionally washing the resulting mixture
(iii) further adding an "Immobilizing Agent" as described above in the section entitled 'Immobilizing Agent'; and
(iv) optionally washing the resulting mixture.

Alternatively, the order of the steps can be:
(i) mixing the immobilizing agent as described above in the section entitled 'Immobilizing Agent', with a radioactive isotope as described above in the section entitled 'Radioactive Isotope';
(ii) further adding the polymer as described above in the section entitled 'Polymer'; and
(iii) optionally washing the resulting mixture.

In one embodiment the radioisotope is added in an acidic solution. In one embodiment the radiolabel is added in a 0.05 M HCl solution. In one embodiment the process includes an additional step of adjusting the pH of the suspension to neutral. In one embodiment the pH of the suspension is adjusted to neutral with 0.05 M NaOH solution.

In one embodiment the concentration of the immobilizing agent is between about 0.5 to 100 µg/mg of polymer. In another embodiment the concentration of the immobilizing agent is between about 1 to 50 µg/mg of polymer. In a further embodiment the concentration of the immobilizing agent is between about 5 to 30 µg/mg of polymer. In another embodiment the concentration of the immobilizing agent is between about 10 to 30 g/mg of polymer. In a further embodiment the concentration of the immobilizing agent is about 20 g/mg of polymer.

In one embodiment the process to prepare the radiolabelled material the process includes the additional steps:
(v) autoclaving the resulting mixture in water or saline and submitting to a sterilization cycle;
(vi) optionally washing the resulting mixture; and
(vii) optionally resuspending the resulting mixture in solution.

In one embodiment of step (v) the resulting mixture is autoclaved in water. In another embodiment of step (v) the resulting mixture is autoclaved in saline.

The present invention also provides for use of an immobilizing agent to immobilize a radioactive isotope on or in a polymer, wherein the immobilizing agent, the radioactive isotope and the polymer are as described above.

The present invention also provides for dual radiolabelled material. In one embodiment the polymer is mixed with a first immobilizing agent and a second immobilizing agent. In one embodiment the first and second immobilizing agents are mixed with the polymer simultaneously. In another embodiment the first and second immobilizing agents are mixed with the polymer sequentially. In one embodiment the first immobilizing agent immobilizes a first radioactive agent and the second immobilizing agent immobilizes a second radioactive agent.

Therapeutic Uses of the Radiolabelled Material

The radiolabelled material may be used to accumulate a therapeutic isotope at a pre-determined disease site in vivo, based on the specific biological interaction that the macromolecule has with a disease marker. In one embodiment the target disease site is the lung. In one embodiment the radiolabelled material of the present invention comprises a macromolecule with strong lung avidity, such as a polycation selected from PDL and PLO.

Selective Internal Radiation Therapy (SIRT) involves the administration of polymer microspheres into the arterial blood supply of the target organ via a catheter and therefore delivers targeted, internal irradiation therapy directly to the tumour. Preferably, the microspheres lodge in the vasculature of the tumour. This provides the advantage that the radiation is preferentially delivered in a slow and continuous manner to the target organ. It is also possible to manipulate the blood supply using appropriate drugs, in order to increase the level of radiation to the target organ (rather than surrounding healthy tissues). As previously mentioned, the immobilizing agent of the present invention substantially prevents leaching and so once the microspheres have reached the target organ, the appropriate radiation is delivered to the tumour.

The administration of polymer microspheres into the arterial blood supply of the target organ via a catheter is, however, an invasive procedure. In preferred embodiments of the radiolabelled material of the present invention the radiolabelled material has high specificity for the lung. In one embodiment the radiolabelled material of the present invention can be administered intravenously to target the lung for treatment of lung cancer, a far less invasive mode of administration. As all veins return blood to the right side of the heart, and the blood is then directed through the pulmonary artery to the lungs, any radiolabelled material that is administered intravenously ultimately enters the arterial supply to the lung, thus allowing for the radiolabelled material to be delivered to and retained in the lungs without entering the left-side of the heart where it would be output to the rest of the body.

In one embodiment of the present invention the radiolabelled material has a high specificity for retention in the lung, minimising any damage to other organs. In one embodiment the radiolabelled material has greater than 90% retention in the lung and less than 10% of the administered dose reaches the liver following the intravenous administration of the radiolabelled material. In another embodiment the radiolabelled material is not detected in the liver following the intravenous administration of the radiolabelled material.

In order to be therapeutically useful in the treatment of lung cancer it is necessary for the radiolabelled material to be retained in the lung for a long enough time period to provide a therapeutic dose of radiation. In one embodiment greater than 50% of the radiolabelled material is retained in the lungs for up to 2 days from the intravenous administration of the radiolabelled material. In another embodiment greater than 50% of the radiolabelled material is retained in the lungs for up to 3 days from the intravenous administration of the radiolabelled material. In a further embodiment greater than 50% of the radiolabelled material is retained in the lungs for up to 4 days from the intravenous administration of the radiolabelled material. In another embodiment greater than 50% of the radiolabelled material is retained in the lungs for up to 5 days from the intravenous administration of the radiolabelled material.

In one embodiment the radiolabelled material is dispersed to the finest vessels of tumour angiogenesis, while still being retained in the lungs.

When targeting the lung it is necessary to ensure that the mass of radiolabelled material administered has no significant impact on lung function, i.e. respiration. In one embodiment of the present invention a therapeutic dose of the radioactive isotope, in particular Lu-177, can be carried in a small enough mass of the radiolabelled material so as to have no impact on lung function.

In further embodiments the radiolabelled material according to the invention can be administered to other internal organs, such as the liver. This has relevance to any potential clinical use of the internal radiation therapy for treating liver tumours, or tumours present in other internal organs.

In further embodiments the radiolabelled material according to the invention can be administered to subcutaneous tumours or other solid tumours that are either superficial on the body or readily accessible by surgery by direct injection into the tumour.

The present invention also provides for use of a radiolabelled material according to the invention and as described above for the manufacture of a medicament for the treatment of cancer and/or for radiation imaging. In one embodiment the cancer is primary or secondary lung cancer.

The present invention also provides a method of radiation therapy of a patient, the method comprising administering to said patient a therapeutically effective amount of a radiolabelled material of the first aspect of the invention.

In one embodiment the radiation therapy is internal radiation therapy for the lung. For example, the radiation therapy is for the treatment of primary and/or metastatic lung tumours.

The present invention further provides for a method for the treatment of cancer, the method comprising administering an effective amount of the radiolabelled material according to the invention and as described above to a patient in need thereof.

The cancer may be a primary sarcoma, a primary or secondary melanoma, a primary head and neck cancer, a primary or secondary brain cancer, a primary or secondary lung cancer, a primary or secondary liver cancer, a primary or secondary breast cancer, a primary or secondary kidney cancer (renal carcinoma), a primary or secondary ovarian cancer, a primary or secondary prostate cancer or a neuroendocrine cancer.

In one embodiment of the methods of the present invention the radiolabelled material according to the invention is administered by intravenous injection.

In another embodiment of the methods of the present invention the radiolabelled material according to the invention is administered by direct intra-tumour injection.

In one embodiment the cancer is a primary or secondary lung cancer.

A preferred example for intravenous injection therapy of primary lung cancer or metastatic tumours in the lung is an 8 micron diameter polystyrene sulfonate microsphere coated with an immobilizing agent comprising PLO with pendant side chains of DTPA chelator and with loading of Lu-177 or Y-90 isotope to provide beta particle irradiation of the tumour.

A preferred example for direct intra-tumour injection therapy of solid tumours that are either superficial on the body or readily accessible by surgery is a 1 micron diameter polystyrene sulfonate microsphere coated with an immobilizing agent comprising PLO with pendant side chains of DTPA chelator and with loading of Lu-177 or Y-90 isotope to provide beta particle irradiation of the tumour.

The present invention also provides a method of imaging a medical procedure in a patient, the method comprising administering to said patient the radiolabelled material according to the invention, and detecting said radiolabelled material in said subject.

In one embodiment the detecting comprises gamma camera imaging of said radioactivity.

The present invention further provides for a medical device comprising a radiolabelled material according to the invention and as described above.

The medical device may be a microsphere, seed, stent, catheter, wire or wafer.

In one embodiment, the radiolabelled material of the invention may be administered by injection. In the case of injectable solutions, the carrier can be a solvent or dispersion medium containing, for example, water, ethanol, polyol (for example, glycerol, propylene glycol, and liquid polyetheylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by including various anti-bacterial and/or anti-fungal agents. Suitable agents are well known to those skilled in the art and include, for example, parabens, chlorobutanol, phenol, benzyl alcohol, ascorbic acid, thimerosal, and the like. In many cases, it may be preferable to include isotonic agents, for example, sugars, polyalcohols such as mannitol, sorbitol, sodium chloride in the composition.

Prolonged absorption of the injectable compositions can be brought about by including in the composition an agent which delays absorption, for example, aluminium monostearate and gelatin.

In one embodiment the radiolabelled material of the invention is administered by intravenous injection. Suitable vehicles for intravenous administration include isotonic saline, 5% dextrose, Hartmann's solution, Hank's balanced salt solution or similar solutions suitable for intravenous use known to those skilled in the art.

In one embodiment the radiolabelled material is administered by intra-peritoneal injection to introduce radiolabelled material into the peritoneal cavity of the body. In one embodiment the introduction of radiolabelled material into the peritoneal cavity of the body can be used to treat disseminated tumour cells from remote primary tumour sites that are populating the peritoneal cavity as ascites and establishing metastases on the outside of abdominal viscera.

In one embodiment the disseminated tumour cells are disseminated ovarian cancer cells. It is a common problem in palliative cancer treatment to retard hyperplasia of ascites and thus alleviate the significant symptoms of cancer growing in the abdominal cavity. In one embodiment the radiolabeled material of the present invention, when injected into the peritoneal cavity, can assist in the alleviation of these symptoms.

In one embodiment, for the treatment of tumours in organs other than the lung, the radiolabelled material is administered intra-arterially. For example, for the treatment of liver tumours, the radiolabelled material is administered intra-arterially to the liver. Suitable vehicles for intra-arterial injection include isotonic saline, 5% dextrose, Hartmann's solution, Hank's balanced salt solution or similar solutions suitable for intravenous use known to those skilled in the art.

In one embodiment, for example where the solid tumours are subcutaneous, superficial on the body, or readily accessible by surgery, the radiolabelled material of the invention is administered by direct injection to the tumour, that is, the radiolabelled material of the invention is administered intratumorally. Suitable vehicles for direct injection to the tumour include isotonic saline, 5% dextrose, Hartmann's solution, Hank's balanced salt solution or similar solutions suitable for intravenous use known to those skilled in the art.

Single or multiple administrations of the radiolabelled material according to the invention may be carried out. In one embodiment the radiolabelled material according to the invention is suitable for fractionated and graded repeat doses. One skilled in the art would be able, by routine experimentation, to determine effective, non-toxic dosage levels of the radiolabelled material of the invention and an administration pattern which would be suitable for treating the diseases and/or infections to which the radiolabelled material are applicable.

Further, it will be apparent to one of ordinary skill in the art that the optimal course of treatment, such as the number of doses of radiolabelled material of the invention given per day for a defined number of days, can be ascertained using conventional course of treatment determination tests.

Generally, an effective dosage per 24 hours may be in the range of about 0.0001 mg to about 1000 mg per kg body weight; for example, about 0.001 mg to about 750 mg per kg body weight; about 0.01 mg to about 500 mg per kg body weight; about 0.1 mg to about 500 mg per kg body weight; about 0.1 mg to about 250 mg per kg body weight; or about 1.0 mg to about 250 mg per kg body weight. More suitably, an effective dosage per 24 hours may be in the range of about 1.0 mg to about 200 mg per kg body weight; about 1.0 mg to about 100 mg per kg body weight; about 1.0 mg to about 50 mg per kg body weight; about 1.0 mg to about 25 mg per kg body weight; about 5.0 mg to about 50 mg per kg body weight; about 5.0 mg to about 20 mg per kg body weight; or about 5.0 mg to about 15 mg per kg body weight. In one embodiment an effective dosage per 24 hours may be in the range of about 1.0 mg to about 10 mg per kg body weight; or about 3.0 to about 5 mg per kg body weight.

Radiolabelled materials in accordance with the present invention may be administered as part of a therapeutic regimen with other drugs. It may be desirable to administer a combination of active compounds, for example, for the purpose of treating a particular disease or condition. Accordingly, it is within the scope of the present invention that two or more pharmaceutical compositions, at least one of which contains a radiolabelled material of the invention, may be combined in the form of a kit suitable for co-administration of the compositions.

The description herein is illustrated by reference to preferred embodiments and examples. On the basis of the description herein the skilled addressee will appreciate that where alternatives are used appropriate conditions may be determined empirically, such alternatives including the radioactive isotope, the immobilizing agent, and the polymer.

The invention will now be described in greater detail, by way of illustration only, with reference to the following non-limiting examples. The examples are intended to serve to illustrate the invention and should not be construed as limiting the generality of the disclosure of the description throughout this specification.

EXAMPLES

Example 1: Synthesis of a Polymeric DTPA-PLO Immobilizing Agent

Diethylenetriamine pentaacetic acid (DTPA) was covalently conjugated to random primary amino groups along the poly-L-ornithine backbone (PLO, Sigma P4538; molecular weight 5-15 kD), using the 1-ethyl-3-(3-dimethylaminopropyl) carbodiimide (EDC) coupling method (Hermanson, G. T., 2013. Bioconjugate Techniques, Academic Press). For example, PLO (10 mg/mL, 500 µL) was added to a solution of DTPA (20 mM), EDC (20 mM), and sulfo-NHS (10 mM, N-Hydroxysulfosuccinimide) in phosphate buffer pH 7 (0.02 M, 500 µL). The solution was mixed at room temperature for 2 hours and then purified through a PD-10 desalting column (GE Healthcare 17-0851-01).

FIG. 1 shows a representation of a polymeric immobilizing agent, based on DTPA covalently linked to PLO. The PLO backbone is represented by the coil on the left with pendant substituents of DTPA linked through an amide linkage. Amino groups of PLO that have not been substituted are free to accept protons and form a positive charge as indicated.

Figure 2:
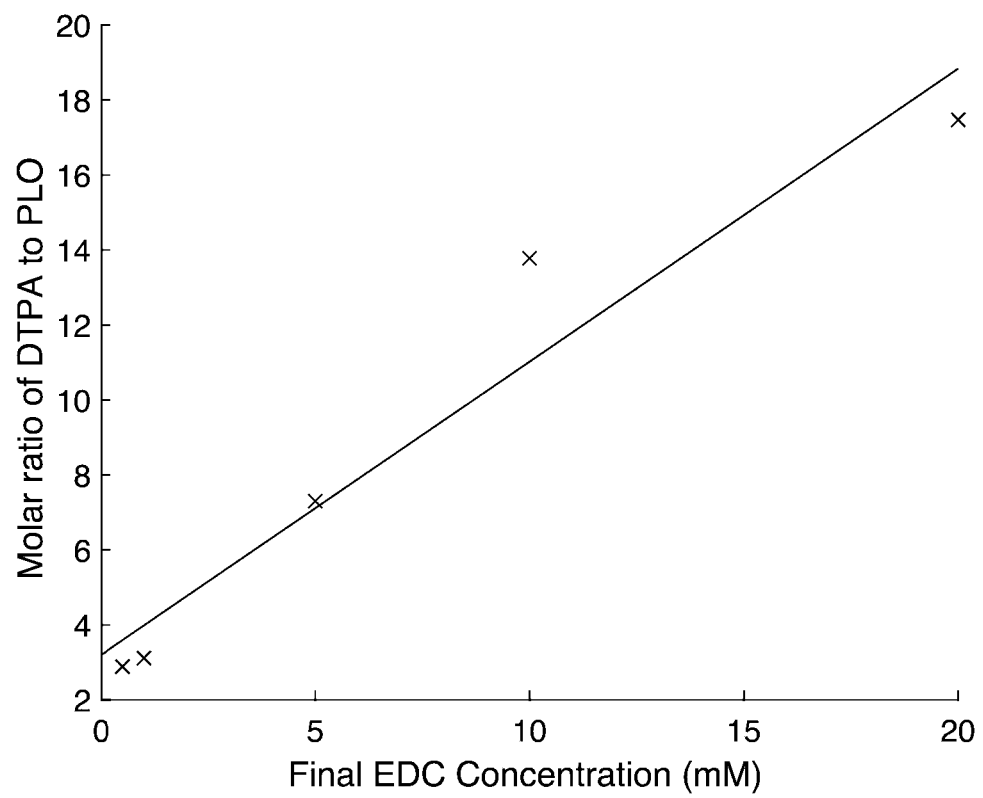
FIG. 2 shows the molar ratios of DTPA to PLO, with regard to a 5 kD molecular weight for PLO, for five constructs prepared with different reagent concentrations. (NB. 5 kD PLO polymer contains 43-44 ornithine residues).

By altering the concentration of the linking reagents (EDC) while keeping all other reaction conditions constant five different DTPA-PLO constructs with different molar ratios of the metal chelating agent to the polycation were prepared (FIG. 2).

Example 2: Calculating the Molar Ratio of DTPA to PLO for the Immobilizing Agent The complexometric indicator Xylenol orange (XO) and its coloured complex with $Fe^{3+}$ (C. Gay, J. Collins, J. M. Gebicki, Determination of iron in solutions with the ferric-xylenol orange complex, Anal. Biochem. 273 (1999) 143-148. doi:10.1006/abio.1999.4207) was used to determine the molar ratio of the linked chelator (DPTA) to the polycation polymer (PLO). Known concentrations of the chelate-polycation were added to a known concentration of $FeCl_3$ solution, and the free $Fe^{3+}$ was determined by the formation of the coloured XO:$Fe^{3+}$ complex. The sample absorbance's were related to a standard curve of the XO:$Fe^{3+}$ complex, which is linear with respect to concentrations of $Fe^{3+}$ in the µM range.

Example 3: Adding a Fluorescent Tag to the Polymeric DTPA-PLO Immobilizing Agent The polymeric DTPA-PLO immobilizing agent may be covalently labeled with other reporter molecules. For example, a fluorescent tag, fluorescein, can be conjugated through a reaction with fluorescein isothiocyanate (FITC, Sigma F4274). Briefly, DTPA-PLO (1.4 mg/mL, 500 µL) was added to a solution of FITC (0.1 mg/mL) in carbonate buffer pH 9 (0.02 M, 500 µL). The solution was left overnight at 4° C., and the reaction was stopped by the addition of 1 M ammonium chloride (50 µL). The fluorescently labeled polycation was purified through a PD-10 desalting column (GE Healthcare 17-0851-01).

Example 4: Quantitating the Binding of the DTPA-PLO Immobilizing Agent to Polystyrene Sulfonate Microspheres The fluorescently labeled DTPA-PLO prepared as in Example 3 above was used to quantify binding of the immobilizing agent to the surface of polystyrene sulfonate microspheres. Various amounts of the fluorescent DTPA-PLO (5, 10, 20, 30 µg) were mixed with the polystyrene sulfonate microspheres (1 mg, 8 am diameter) in either water or saline (1 mL), for 1 h at room temperature. The microspheres were pelleted by centrifugation at 3000 g for 2 min and the fluorescence in the supernatants (200 µL) were each measured in a Varioskan LUX multimode plate reader (ex. 485 nm; em. 525 nm, Thermo Fisher Scientific).

Figure 3:
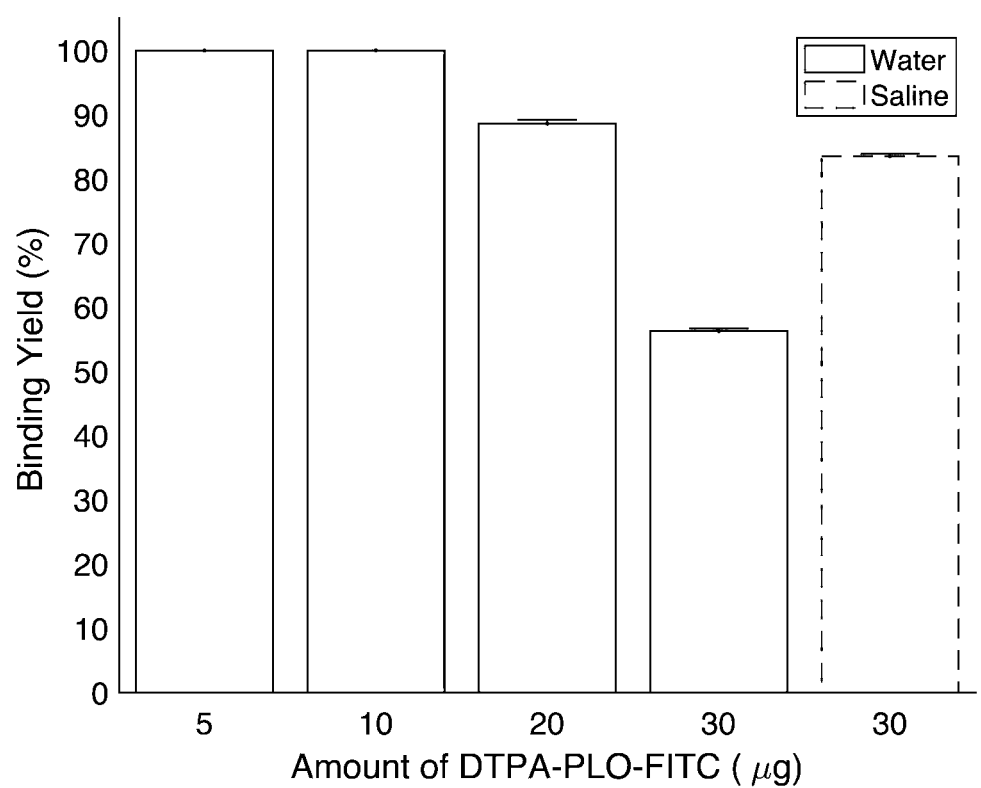
FIG. 3 shows the binding yields for different amounts of the fluorescently labeled DTPA-PLO immobilizing agent after mixing with the polystyrene sulfonate microspheres (1 mg).

FIG. 3 shows the binding yields for different amounts of the fluorescently labeled DTPA-PLO immobilizing agent after mixing with the polystyrene sulfonate microspheres. Complete binding was observed for up to 10 µg of the DTPA-PLO-FITC, mixed with 1 mg of 8 µm microspheres, and saturation appeared to occur at 17-18 µg of the polycation. Notably, the amount of polycation bound could be increased in the presence of saline, perhaps due to interruption of intramolecular bonds between the DTPA carboxylate groups and the PLO amine groups, thus allowing for a more extended conformation of the bound immobilizing agent. This would allow more positively charged groups of the polycation to bind to the negatively charged microsphere, thus resulting in stronger binding. In the presence of saline, saturation of DTPA-PLO-FITC binding to the microspheres was observed at 25 µg, thereby achieving an approximately 39% increase in bound immobilizing agent per mg of microspheres.

Example 5: Preparation of $^{177}$Lu-DTPA-PLO-Microspheres

Table 1 shows an example process for preparation of $^{177}$Lu radiolabelled microspheres.

TABLE 1

| Example preparation of $^{177}$Lu labelled microspheres | |
|---|---|
| Step 1 | 1 mg polystyrene sulfonate microspheres, 1, 8 or 30 µm diameter<br>Washed 3× with 1 mL water (centrifuge at 3000 g for 2 min) |
| Step 2 | Add DTPA-PLO (20 µg/mg microspheres) to the washed microspheres in H$_2$O or saline (1 mL)<br>Mix gently for 1 hour |
| Step 3 | Wash 3× with 1 mL H$_2$O (centrifuge at 3000 g for 2 min.) |

TABLE 1-continued

| Example preparation of $^{177}$Lu labelled microspheres | |
|---|---|
| Step 4 | Microsphere suspension (1 mL) was added to $^{177}$LuCl$_3$ (8 µL in 0.05M HCl; 8.3 MBq)<br>Adjust pH to neutral with 0.05M NaOH (8.1 µL) (Optional)<br>Mix gently for 1 hour at room temperature |
| Step 5 | Wash 3× with 1.0 mL saline<br>Anticipated retention of $^{177}$Lu on microspheres 90-99% |
| Step 6 | Autoclave the microsphere preparation in 1 mL H$_2$O or saline<br>Standard sterilization cycle 121° C., 20 minutes |
| Step 7 | Wash 3× with 1 mL saline<br>Anticipated retention of $^{177}$Lu on microspheres—(water, 95-100%; saline, 70%) |
| Step 8 | Resuspend in 1 mL Hartmann's solution<br>Anticipated retention of $^{177}$Lu after a further 24 h—95% |

Example 6: The Lung Distribution and Safety Impact of Microspheres Injected Intravenously The optimal lung loading of microspheres in vivo, as well as the safety of a repeated lung microsphere loading strategy, was investigated with two cohorts of BALB/c mice. For the first cohort, three groups of 5 healthy mice received a single loading of non-radioactive microspheres (8 µm diameter), intravenously (via a tail vein) in a 5% dextrose solution. The microsphere loading was incrementally increased in the groups from 6 mg/kg, to 9 mg/kg and then 12 mg/kg. The welfare of the mice was carefully monitored every day and the mice were scored (0-3) against several standard mouse model criteria. At 7 days post-injection, the mice were culled and their lungs harvested for histology. Two lungs from each group were sent to an accredited veterinary pathology laboratory for histology and reporting by a qualified pathologist.

The welfare of the mice was carefully monitored and there was no noticeable impact resulting from the intravenous microsphere injections. A summary of the lung histology results is shown in Table 2 and the pathologist's report stated, "Microspheres were widely distributed throughout the lung in the interstitial tissue. There was very little inflammation around the microsphere and mostly no inflammation around the microspheres. The microspheres were randomly dispersed throughout the interstitial tissue and did not appear to cluster around large blood vessels, nor did they cluster adjacent to large airways. I really did not note any obvious difference of the dispersion of the microspheres in mouse 1 to 6. They all seemed to be randomly dispersed and no real difference in the distribution. Perhaps, with increased numbers of microspheres there was some tendency for microspheres to be found in a small cluster of two or three. But this is pretty subjective. There was no obvious inflammation with increased numbers of microspheres."

The second cohort of mice was injected with a fractionated loading of the microspheres with no radioactivity present. The loading was divided and delivered over three intravenous injections of 3 mg/kg, 7 days apart (a total loading of 9 mg/kg), and the mice were monitored for a further 7 days following the last injection. Again, the welfare of the mice was carefully monitored and there was no noticeable impact resulting from the intravenous microsphere injections.

Table 2

| Sample | Microsphere Loading (mg/kg) | Microspheres per 10 high power fields (×40 objective) | Inflammation around microsphere in the interstitial tissue | Other inflammatory changes |
|---|---|---|---|---|
| 1 | 6 | 21 | No significance inflammation | No |
| 2 | 6 | 10 | No significance inflammation | Extracellular haemorrhage, post mortem artefact |

Table 2-continued

| Sample | Microsphere Loading (mg/kg) | Microspheres per 10 high power fields (×40 objective) | Inflammation around microsphere in the interstitial tissue | Other inflammatory changes |
|---|---|---|---|---|
| 3 | 9 | 29 | No significance inflammation | No |
| 4 | 9 | 33 | No significance inflammation | No |
| 5 | 12 | 38 | No significance inflammation | No |
| 6 | 12 | 44 | No significance inflammation | No |

Example 7. The Biodistribution and Elimination of Different $^{177}$Lu Preparations Four groups of 3 BALB/c mice were injected intravenously (via a tail vein) with either a preparation of $^{177}$Lu-DTPA-PLO-microspheres (8 µm; 3 mg/kg; Group 1), $^{177}$Lu-DTPA-PLO with no microspheres (Group 2), $^{177}$Lu bound directly to microspheres with no polymeric immobilizer (3 mg/kg; Group 3), or free $^{177}$LuCl$_3$ (Group 4). After 3 hours, all 12 mice were euthanised and dissected to measure the radioactivity in the lungs, liver, spleen and carcass. The results are shown in Table 3.

Shown in Table 3 is the radioactivity present in lungs, liver/spleen and carcass for the 4 groups of mice that had received the different preparations of the $^{177}$Lu radioisotope; $^{177}$Lu-DTPA-PLO-microspheres (Group 1); $^{177}$Lu-DTPA-PLO with no microspheres (Group 2), $^{177}$Lu bound directly to microspheres with no polymeric immobilizer (Group 3), or free $^{177}$LuCl$_3$ (Group 4). A high level of $^{177}$Lu retention in the lungs (93%) was observed for the $^{177}$Lu-DTPA-PLO-microspheres (Group 1), while the other preparations were not retained in the lungs but were instead found at high levels in the carcass, localised in the skeleton. The $^{177}$Lu bound to microspheres without the polymeric immobilizer (Group 3), had high carcass activity, very similar to that of free $^{177}$LuCl$_3$ (Group 4), demonstrating that the DTPA-PLO immobilizer is essential for high in vivo stability of the labeled microspheres. In addition to uptake in the carcass skeleton, the $^{177}$Lu complexed with DTPA-PLO but without the microspheres (Group 2) was also removed from the blood by the liver/spleen, which contained 32% of the measured activity. However the total counts for Group 2 (873) were, on average, 25% of the other group's total counts, indicating that $^{177}$Lu-DTPA-PLO is mainly eliminated via another route, presumably through the renal system.

Figure 4:
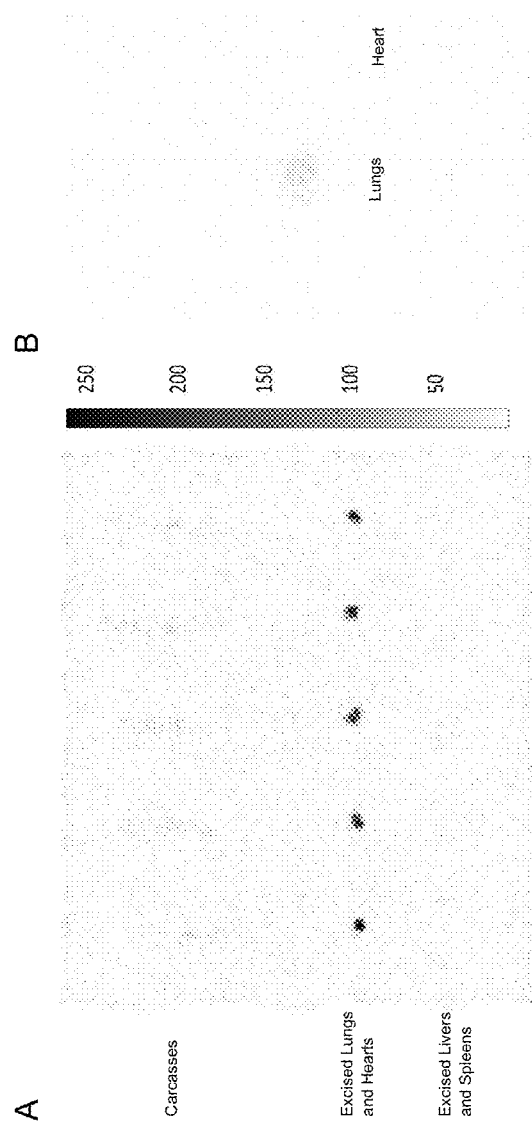
FIG. 4 shows gamma camera images of five dissected mice carcasses after intravenous injection of $^{177}$Lu-DPTA-PLO-microspheres (3 mg/kg). Their excised heart/lungs, livers and spleens shown in FIG. 4A.

Example 8: Stability Test of $^{177}$Lu-DTPA-PLO-Microspheres In Vivo—Long-Term Mouse Lung Retention Test Five BALB/c mice were injected intravenously (via a tail vein) with a preparation of $^{177}$Lu-DTPA-PLO-microspheres (3 mg/kg). The microspheres were 8 µm diameter and loaded with 26 MBq of $^{177}$Lu per milligram, and were injected as a suspension in 5% dextrose solution (0.17 mL) such that each mouse received an average activity of 1.66 MBq. Five days following injection, the mice were euthanised and dissected to measure radioactivity in the lungs, liver and carcass. The dissected mice were imaged with an Infinia Hawkeye 4 SPECT scanner (GE Healthcare), and activity in the lungs was measured with a CRC-Ultra chamber (Capintec). The results are summarized in FIG. 4 and Table 4.

Gamma camera images of the five dissected mice carcasses with their excised heart/lungs, livers and spleens are shown in FIG. 4A. The counts of the images were multiplied by a factor of 20 for visualization. Clearly, even after 5 days post-injection, the retention of the $^{177}$Lu in the heart/lungs is high. Removing the heart from the lungs (FIG. 4B) clearly demonstrated that the microspheres had indeed cleared the heart and lodged in the capillary network of the lungs.

Table 4 shows the radioactivity present in the lungs, liver and carcass of 5 mice, 5 days following the intravenous injection of $^{177}$Lu-DTPA-PLO-microspheres. At 5 days post-injection, 57% of the injected activity was still present in the excised lungs of the mice (time corrected for radioactive decay). Regions of interest from the gamma images (FIG. 4A) showed that of the activity remaining in the mice after 5 days, 79% was present in the lungs, 20% in the carcass and 1% in the liver/spleen (Table 4).

TABLE 3

| Group | MBq Injected | Lung Counts | Lung % Total | Liver/Spleen Counts | Liver/Spleen % Total | Carcass Counts | Carcass % Total | Total Counts |
|---|---|---|---|---|---|---|---|---|
| 1 | 1.32 | 4000 | 98.11 | 8 | 0.20 | 69 | 1.69 | 4077 |
| 1 | 1.38 | 4023 | 96.66 | 5 | 0.12 | 134 | 3.22 | 4162 |
| 1 | 0.55 | 1439 | 84.00 | 1 | 0.06 | 273 | 15.94 | 1713 |
| Mean | 1.08 | 3154 | 92.93 | 5 | 0.12 | 159 | 6.95 | 3317 |
| 2 | 1.55 | 43 | 8.69 | 231 | 46.67 | 221 | 44.65 | 495 |
| 2 | 1.57 | 8 | 0.75 | 237 | 22.30 | 818 | 76.95 | 1063 |
| 2 | 1.55 | 41 | 3.87 | 281 | 26.51 | 738 | 69.62 | 1060 |
| Mean | 1.56 | 31 | 4.44 | 250 | 31.82 | 592 | 63.74 | 873 |
| 3 | 1.52 | 242 | 6.04 | 163 | 4.07 | 3603 | 89.90 | 4008 |
| 3 | 1.31 | 175 | 4.85 | 269 | 7.46 | 3162 | 87.69 | 3606 |
| 3 | 1.06 | 191 | 6.61 | 135 | 4.67 | 2565 | 88.72 | 2891 |
| Mean | 1.30 | 203 | 5.83 | 189 | 5.40 | 3110 | 88.77 | 3502 |
| 4 | 1.53 | 113 | 2.96 | 236 | 6.17 | 3475 | 90.87 | 3824 |
| 4 | 1.56 | 42 | 1.07 | 357 | 9.08 | 3533 | 89.85 | 3932 |
| 4 | 1.56 | 117 | 2.95 | 315 | 7.94 | 3537 | 89.12 | 3969 |
| Mean | 1.55 | 91 | 2.32 | 303 | 7.73 | 3515 | 89.95 | 3908 |

TABLE 4

| Mouse # | Injected Activity (MBq) | Lung Activity (MBq) | Lung Retention % of Injected | Lung Counts | Lung % Total | Average Liver/Spleen counts | Average Liver/Spleen % Total | Carcass Counts | Carcass % Total | Total Counts |
|---|---|---|---|---|---|---|---|---|---|---|
| 1 | 1.65 | 0.40 | 51.33 | 1556 | 75.69 | 26.80 | 1.30 | 473 | 23.01 | 2056 |
| 2 | 1.63 | 0.33 | 55.09 | 1765 | 78.56 | 26.80 | 1.19 | 455 | 20.25 | 2247 |
| 3 | 1.68 | 0.35 | 62.56 | 1818 | 78.61 | 26.80 | 1.16 | 468 | 20.24 | 2313 |
| 4 | 1.64 | 0.37 | 57.87 | 1740 | 78.07 | 26.80 | 1.20 | 462 | 20.73 | 2229 |
| 5 | 1.69 | 0.36 | 59.17 | 1857 | 82.91 | 26.80 | 1.20 | 356 | 15.89 | 2240 |
| Mean | 1.66 | 0.36 | 57.20 | 1747.20 | 78.77 | 26.80 | 1.21 | 442.80 | 20.02 | 2216.80 |

Example 9: Summary of the Average In Vivo Lung Retention in Mice for the $^{177}$Lu-DTPA-PLO-Microspheres and the Absorbed Doses Over the course of a number (n=8) of separate experiments, a total of 64 BALB/c mice have been injected intravenously (via a tail vein) with preparations of $^{177}$Lu-DTPA-PLO-microspheres (3 mg/kg). The microspheres were 8 m diameter, and were injected as a suspension in 5% dextrose solution (0.17 mL) such that each mouse received an average activity of 1.6 MBq. At various time points (24 to 552 hours) post-injection, the mice were euthanised and dissected to measure radioactivity in the lungs, liver and carcass. The dissected mice were imaged with an Infinia Hawkeye 4 SPECT scanner (GE Healthcare), and the activity in the lungs was measured with a CRC-Ultra chamber (Capintec). The results are summarised in Table 5 and FIG. 5.

Table 5 summarises the lung activities and gamma camera counts over time for 64 mice injected with $^{177}$Lu-DTPA-PLO-microspheres. The average activity in the lungs after 5 days post-injection was 53% of the injected activity (time corrected for decay). By 23 days post-injection the average lung retention was still at 16% of the injected activity, but given the half-life of 177Lu is 6.647 days, the actual activity in the lungs was only 1% of that injected.

Figure 5:
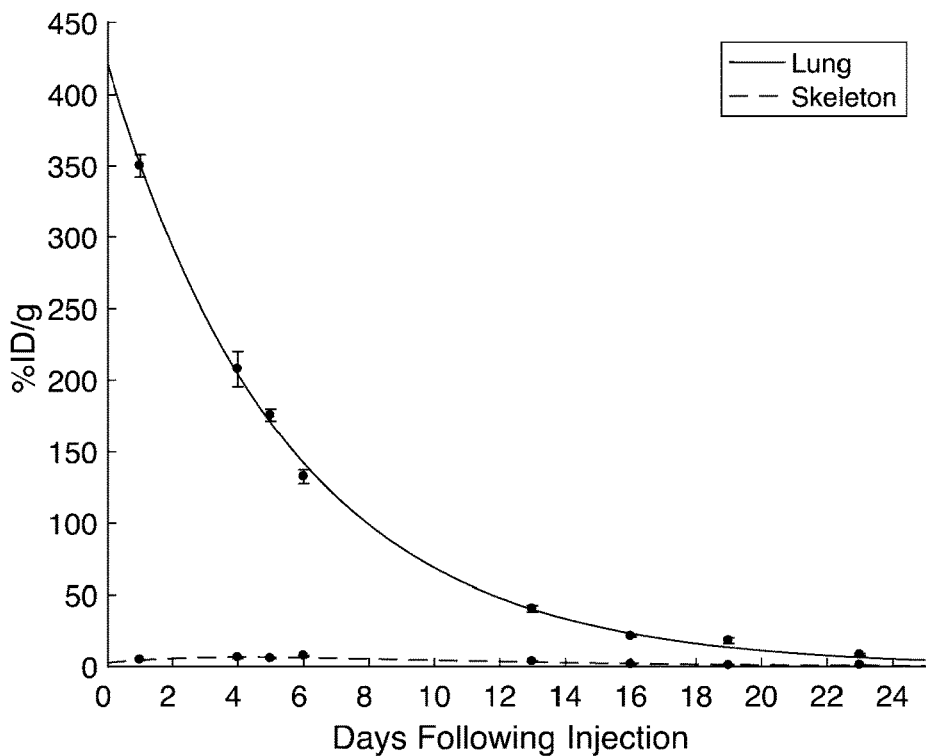
FIG. 5 shows the percent injected dose (% ID) per gram tissue weight for the lungs and the skeleton/carcass following intravenous injection of $^{177}$Lu-DPTA-PLO-microspheres (3 mg/kg).

The data from Table 5 was used to calculate the percent injected dose (% ID) per gram tissue weight for the lungs and the skeleton/carcass (FIG. 5). This was calculated assuming an average tissue wet weight of 0.18 g for the mouse lungs, and a weight of 1.5 g for the mouse skeleton (7.5% of a 20 g mouse; Di Masso, R. J., Celoria, G. C. & Font, M. T., 1998. Morphometric skeletal traits, femoral measurements, and bone mineral deposition in mice with agonistic selection for body conformation. Bone, 22(5), pp. 539-543.). Clearly, the lungs received the majority of the dose per gram of tissue over time. Radiation Absorbed Doses were estimated using the Medical Internal Radiation Dose (MIRD) schema and ignoring the small contribution due to the gamma emissions from $^{177}$Lu. The absorbed dose received by the lung injected with an activity of 1.6 MBq on the $^{177}$Lu-DTPA-PLO-microspheres over 23 days, was estimated to be 75.4 Gray, while the absorbed dose to the skeleton was estimated to be only 2.8 Gray.

TABLE 5

| Time (days) | Number of Mice | Average Lung Activity (MBq) | Average Lung Retention % Injected | Average Lung Counts | Average Lung % Total | Average Carcass Counts | Average Carcass % Counts | Average Total Counts |
|---|---|---|---|---|---|---|---|---|
| 1 | 6 | 1.01 | 69.95 | 3996.83 | 89.45 | 455.41 | 10.25 | 4452.24 |
| 4 | 5 | 0.60 | 56.78 | 2137.60 | 79.42 | 555.24 | 20.58 | 2692.84 |
| 5 | 29 | 0.51 | 53.19 | 1588.95 | 77.77 | 430.16 | 21.42 | 2019.10 |
| 6 | 10 | 0.38 | 44.59 | 1035.80 | 66.18 | 497.80 | 32.00 | 1533.60 |
| 13 | 3 | 0.12 | 28.20 | 385.00 | 57.36 | 286.67 | 42.64 | 671.67 |
| 16 | 3 | 0.06 | 20.31 | 281.00 | 61.79 | 175.33 | 38.21 | 456.33 |
| 19 | 4 | 0.05 | 23.79 | 451.75 | 74.23 | 131.00 | 25.77 | 582.75 |
| 23 | 4 | 0.02 | 16.69 | 93.50 | 44.75 | 116.00 | 55.25 | 209.50 |

Example 10: The Effect of the DTPA to PLO Molar Ratio of the Immobilizing Agent on In Vivo Mouse Lung Retention Several different DTPA-PLO constructs were synthesized with different molar ratios of DTPA to PLO (Example 1). Three of these polymers with DTPA to PLO molar ratios of 17.5, 13.8 and 7.3 were used to construct three $^{177}$Lu-DTPA-PLO-microsphere preparations (8 μm diameter). These were injected into three groups of four BALB/c mice intravenously (via a tail vein) as a suspension in 5% dextrose solution (0.15 mL) such that each mouse received an average activity of 0.9 MBq. Four days following injection, the mice were euthanised and dissected to measure radioactivity in the lungs with a CRC-Ultra chamber (Capintec). The lung retention results are summarised in Table 6.

The results in Table 6 indicate that the higher molar ratios of DTPA to PLO are needed to give high retention of the radioisotope ($^{177}$Lu) in the lungs of mice over four days. The molar ratio of 13.8 resulted in the highest retention of the injected activity at 57%. Increasing the molar ratio slightly decreased the retention. However, the molar ratio of 7.3 resulted in the retention of only 5% of the injected activity over the 4 days. There appears to be an optimal ratio of DTPA to the PLO polycation, whereby there are sufficient DTPA molecules to retain the $^{177}$Lu, yet at the same time provide sufficient numbers of free amine groups on the PLO to facilitate strong binding of the immobilizing agent to the polystyrene sulfonate microsphere. Constructs with molar ratios of 3 (FIG. 2) did not perform well even in in vitro stability tests, where they failed to retain the $^{177}$Lu on the microspheres in the presence of Hartmann's solution, which mimics the 2 mM $Ca^{2+}$ present in blood plasma.

Table 6

| Molar ratio of DTPA to PLO | Isotope Binding Yield | Average in vivo Lung Retention % Injected (n = 4) ± sem |
|---|---|---|
| 17.5 | 93.7 | 47.3 ± 2.6 |
| 13.8 | 90.7 | 56.8 ± 3.3 |
| 7.3 | 94.6 | 5.0 ± 1.3 |

Example 11: Optimization of Sterilization Conditions

A sterile 177Lu-DTPA-PLO-microsphere preparation can be produced following the method in Example 5 starting from sterile materials and using sterile technique (Steps 1-5). It would be advantageous, however, if the complete preparation was stable to standard autoclaving conditions (Step 6, Example 5) and still provided high in vivo retention. It would be a requirement for any clinical use of such a preparation that the final preparation was sterilized by autoclaving prior to distribution and intravenous injection into patients. The in vivo lung retention of four different sterile preparations in BALB/c mice is summarized in FIG. 6 as the percent injected dose per gram wet weight of tissue, and at various time points. Data for the $^{177}$Lu-DTPA-PLO-microspheres prepared under sterile conditions are shown as crosses, with a fitted exponential curve (data from Example 8). In addition to these data three different autoclaved $^{177}$Lu-DTPA-PLO-microsphere preparations were produced. Firstly (+data points), $^{177}$Lu-DTPA-PLO-microspheres were prepared with steps 2 and 6 performed in water (Example 5). Secondly (triangle data points), $^{177}$Lu-DTPA-PLO-microspheres were prepared with step 2 performed in water, and step 6 performed in saline (Example 5). Thirdly (circle data points), $^{177}$Lu-DTPA-PLO-microspheres were prepared with both steps 2 and 6 performed in saline (Example 5). These three $^{177}$Lu-DTPA-PLO-microsphere preparations were injected intravenously (via a tail vein) into three groups of 10 BALB/c mice as a suspension in saline (0.17 mL) such that each mouse received an average activity of 1.3 MBq. At 6 days post-injection, 5 mice from each group were euthanised and dissected to measure radioactivity in the lungs with a CRC-Ultra chamber (Capintec). At 12 days following injection, this was repeated for the remaining 5 mice in each group.

Figure 6:
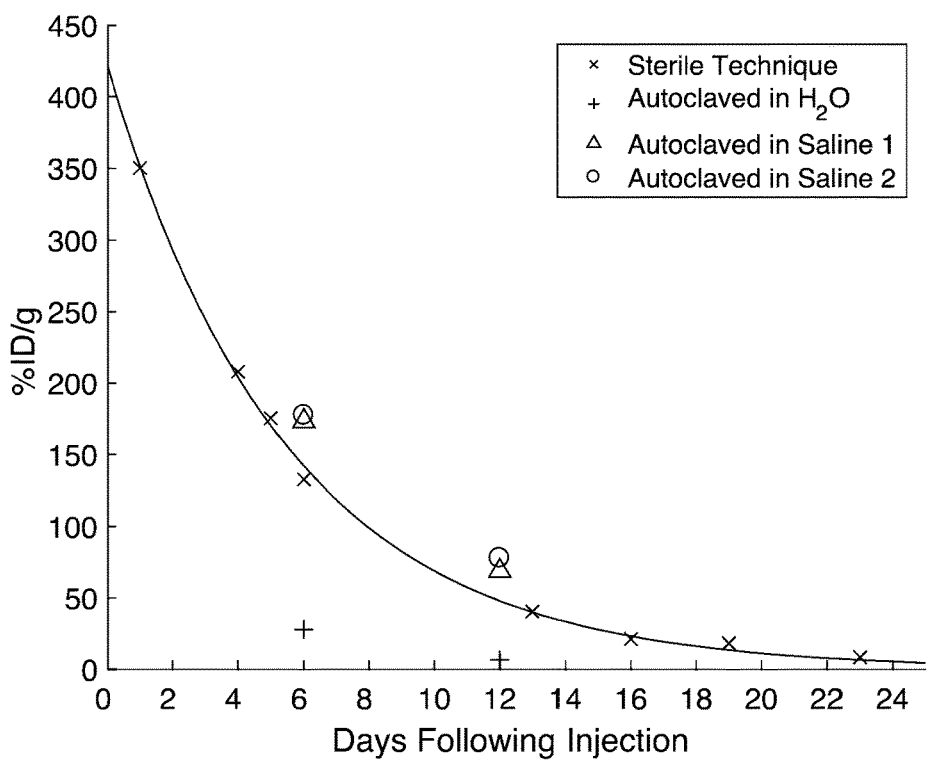
FIG. 6 shows that there was an increased level of activity in the lungs of mice that had received $^{177}$Lu-DPTA-PLO-microsphere preparations autoclaved in saline, compared to the activity found in the lungs of mice that had received $^{177}$Lu-DPTA-PLO-microsphere preparations autoclaved in water.

FIG. 6 shows that there was an increased level of activity found in the lungs of mice that had received preparations autoclaved in saline, compared to the activity found in the lungs of mice that had received preparations autoclaved in water; this increase was maintained over the time course of the experiment. These results indicated that autoclaving the microsphere preparations in saline is a preferred method of sterilization.

Example 12: Growth of the Mouse 4T1-Luc2 Breast Cancer Cell Line in Mouse Lungs

Figure 7:
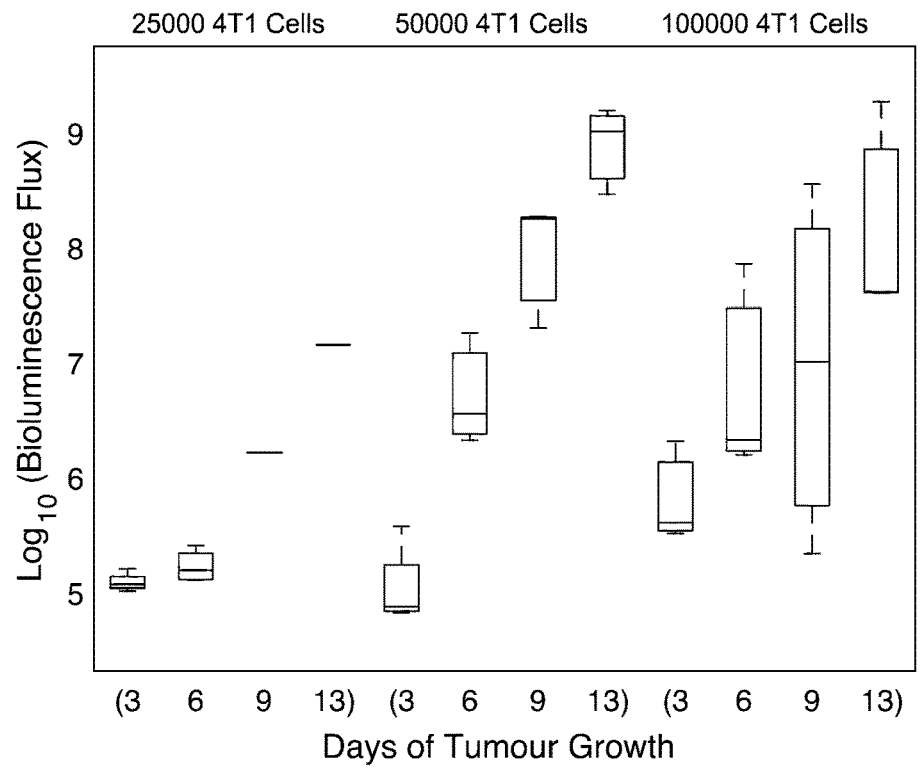
FIG. 7 shows the bioluminescence flux measurements from the lungs of mice injected with 25000, 50000, or 100000 4T1-luc2 cells intravenously (via a tail vein) in Hank's balanced salt solution. Lung tumour growth was measured on days 3, 6, 9 and 13 post injection of the cells. The mice were injected intraperitoneally (IP) with luciferin and the mice were anaesthetised and the lung bioluminescence was measured with an IVIS Spectrum in vivo imaging system.

The mouse 4T1-luc2 breast cancer cell line is a commonly used lung metastasis model as it is possible to non-invasively image tumour growth in vivo. The cell line has been transfected with the firefly luciferase gene (luc2), so that in the presence of luciferin, viable cells produce light that can be detected with a bioluminescence camera. To begin investigations with this lung metastasis model, 12 BALB/c mice were divided into three groups and injected with 25000, 50000, or 100000 4T1-luc2 cells, intravenously (via a tail vein) in Hank's balanced salt solution (150 μL). Lung tumour growth was measured on days 3, 6, 9 and 13, post-injection of cells. Briefly, the mice were injected intraperitoneally (IP) with the luciferase substrate, luciferin, and the mice were then anaesthetised and the lung bioluminescence measured with an IVIS Spectrum in vivo imaging system (PerkinElmer). The bioluminescence flux measurements from the lungs of the mice are shown in FIG. 7. The injection of 50000 cells was found to produce a growth curve over a convenient range of bioluminescence flux and this number of cells was adopted for further experimental investigations.

Example 13. The Effect of Internal Radiation from $^{177}$Lu-DTPA-PLO-Microspheres on the Growth of Mouse 4T1-Luc2 Tumours in Mouse Lungs Tumours were grown in the lungs of 18 BALB/c mice by injecting 4T1-luc2 cells (50000 cells) intravenously (via a tail vein). At 5 days of tumour growth the lung bioluminescence was measured with an IVIS Spectrum in vivo imaging system (PerkinElmer) and the mice were divided into two groups; a treatment group (n=9), and a negative control group (n=9) bearing approximately equal total tumour burdens. The mice in the treatment group were then injected intravenously (via a tail vein) with a preparation of $^{177}$Lu-DTPA-PLO-microspheres (3 mg/kg), such that each mouse received an average activity of 1.59 MBq. Mice in the negative control group were injected with a non-radioactive $^{175}$Lu-DTPA-PLO-microsphere preparation (3 mg/kg). The microspheres were 8 μm diameter and were injected as a suspension in 5% dextrose solution (0.17 mL). At 11 days of growth (after 6 days of exposure to internal radiation), the tumour bioluminescence was measured and the results are shown in FIG. 8.

Figure 8:
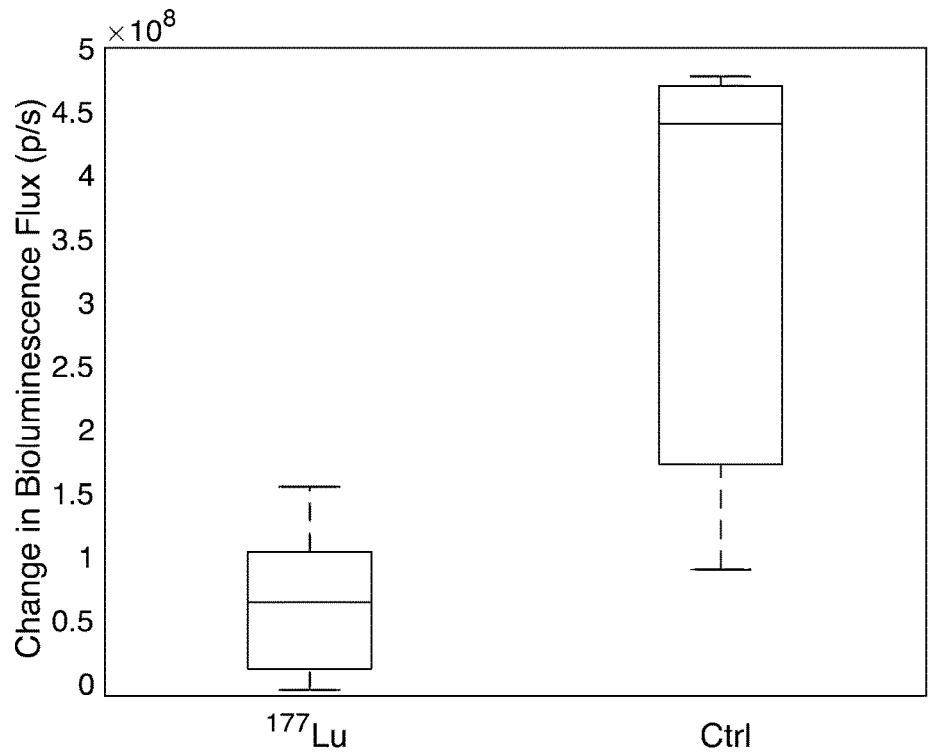
FIG. 8 shows the effect of internal ionizing radiation from $^{177}$Lu-DPTA-PLO-microspheres on the growth of mouse lung 4T1-luc2 tumours. The results are shown for two groups of mice; the treated group ($^{177}$Lu), which received $^{177}$Lu-DTPA-PLO-microspheres; and the negative control group (Ctrl), which received $^{175}$Lu-DTPA-PLO-microspheres.

Shown in FIG. 8 is the effect of the internal ionizing radiation from $^{177}$Lu-DTPA-PLO-microspheres on the growth of mouse lung 4T1-luc2 tumours. The results are shown for two groups of mice; the treated group ($^{177}$Lu), which received $^{177}$Lu-DTPA-PLO-microspheres; and the negative control group (Ctrl), which received $^{175}$Lu-DTPA-PLO-microspheres. The treated mice showed a statistically significant reduction in tumour growth (p=0.0012) between days 5 and 11, as measured by the decreased change in bioluminescence flux produced by the luciferase-transfected tumour cells. The negative control group had a median change in bioluminescence 6.58 times larger than the treated group.

Example 14: Improved Survival to Welfare End-Point Using $^{177}$Lu-DTPA-PLO-Microspheres to Retard the Growth of Mouse Lung 4T1-Luc2 Tumours Tumours were grown in the lungs of 20 BALB/c mice by injecting 4T1-luc2 cells (50000 cells) intravenously (via a tail vein). At 5 days of tumour growth the lung bioluminescence was measured with an IVIS Spectrum in vivo imaging system (PerkinElmer) and the mice were divided into two groups; a treatment group, and a negative control group bearing approximately equal total tumour burdens. The mice in the treatment group were then injected intravenously (via a tail vein) with a preparation of $^{177}$Lu-DTPA-PLO-microspheres (3 mg/kg), such that each mouse received an average activity of 1.59 MBq. Mice in the negative control group were injected with a non-radioactive $^{175}$Lu-DTPA-PLO-microsphere preparation (3 mg/kg). The microspheres were 8 μm diameter and were injected as a suspension in 5% dextrose solution (0.17 mL). The welfare of the mice was carefully monitored every day and the mice were scored (0-3) against several standard mouse model criteria. The people scoring the mice were unaware of which mice were assigned to each group, and if a total score greater than or equal to 3 was reached, over all criteria, then lung bioluminescence was immediately measured and the animal was culled. Common criteria that often contributed to the end-point were coat appearance, activity, movement, breathing, and body weight. The time point at which the mice were culled was used to estimate survival functions for the two groups, which are shown in FIG. 9.

Figure 9:
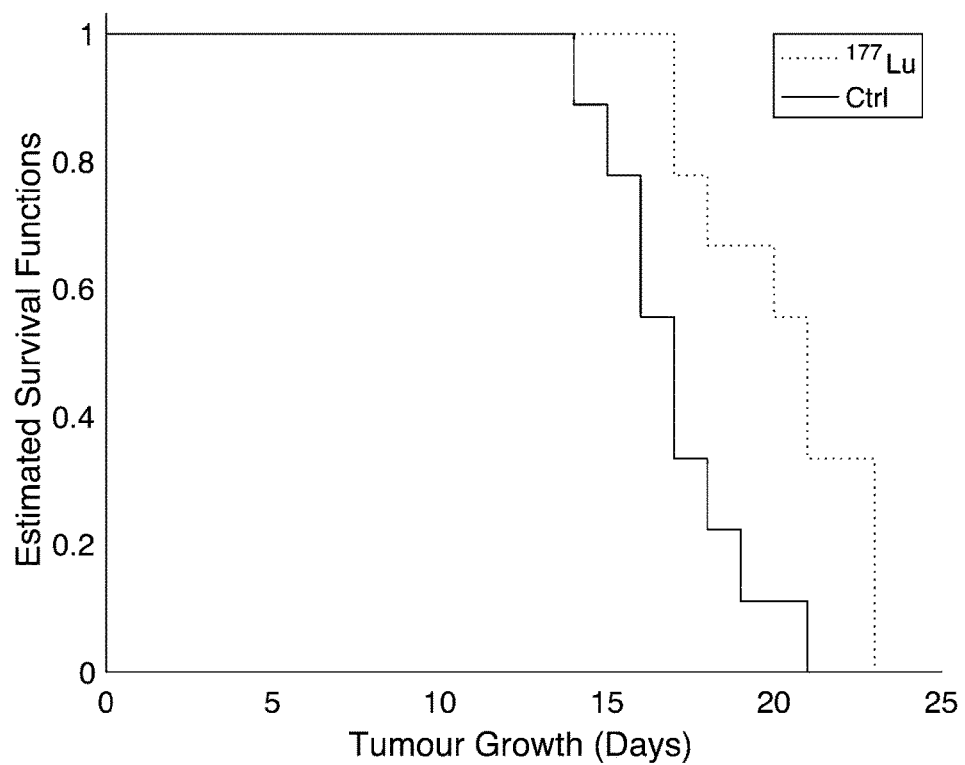
FIG. 9 shows the improved survival to welfare end-point using $^{177}$Lu-DTPA-PLO-microspheres to retard the growth of mouse lung 4T1-luc2 tumours.

The survival function shown in FIG. 9, clearly show that the internal radiation therapy of the mouse lung tumours produced a prolongation of survival of mice to the welfare end-point. The median difference in survival was 4 days, which was statically significant (p=0.02).

Example 15: The Effect of Internal Radiation at Different Doses on the Growth of Mouse 471-Luc2 Tumours in Mouse Lungs The effect on the growth of mouse lung tumours exposed to different radioactivities on the $^{177}$Lu-DTPA-PLO-microspheres was investigated. Tumours were grown in the lungs of 40 BALB/c mice by injecting 4T1-luc2 cells (50000 cells) intravenously (via a tail vein). At 5 days of tumour growth the lung bioluminescence was measured with an IVIS Spectrum in vivo imaging system (PerkinElmer) and the mice were divided into four groups; a negative control group (n=10), and a three treatment groups (3×n=10) bearing approximately equal total tumour burdens. The mice in the three treatment groups were then injected intravenously (via a tail vein) with a preparation of $^{177}$Lu-DTPA-PLO-microspheres (3 mg/kg), such that each mouse received an average activity of 0.82, 1.1 or 1.37 MBq. Mice in the negative control group were injected with a non-radioactive $^{175}$Lu-DTPA-PLO-microsphere preparation (3 mg/kg). The microspheres were 8 µm diameter and were injected as a suspension in 5% dextrose solution (0.17 mL). At 11 days of growth (after 6 days of exposure to internal radiation), the tumour bioluminescence was measured and the results are shown in FIG. 10.

Figure 10:
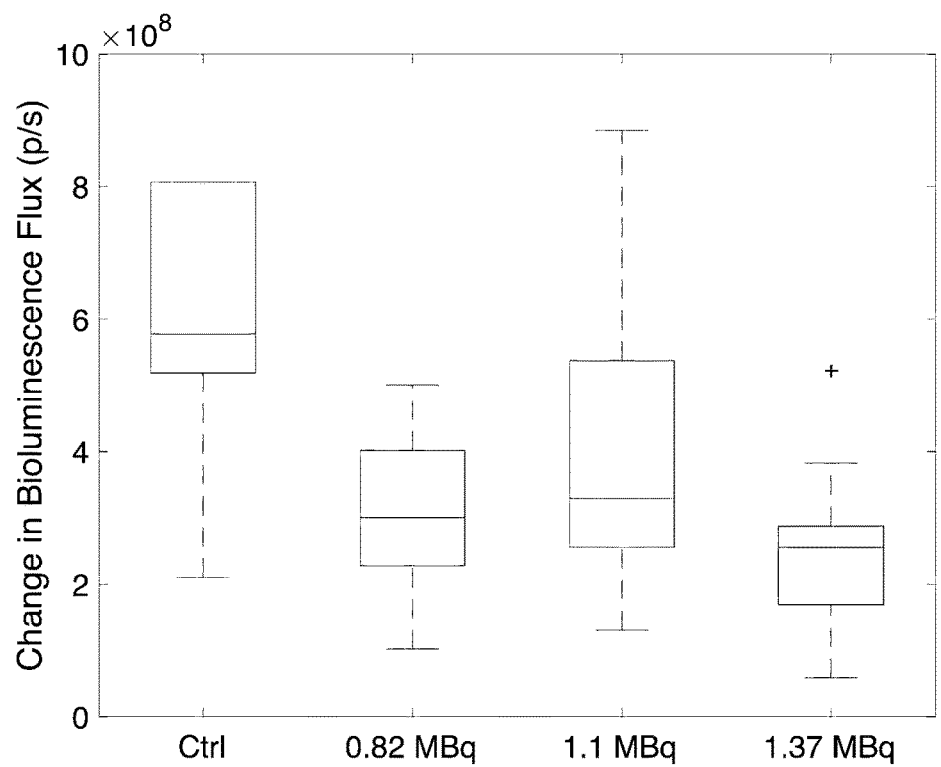
FIG. 10 shows the effect of three different doses of internal ionizing radiation from $^{177}$Lu-DTPA-PLO-microspheres on the growth of mouse lung 4T1-luc2 tumours. The results are shown for four groups of mice; the negative control group (Ctrl), which received $^{175}$Lu-DTPA-PLO-microspheres; and three treated groups, which received $^{177}$Lu-DTPA-PLO-microspheres with radioactivities of 0.82, 1.1, and 1.37 MBq.

Shown in FIG. 10 is the effect of three different doses of internal ionizing radiation from $^{177}$Lu-DTPA-PLO-microspheres on the growth of mouse lung 4T1-luc2 tumours. The results are shown for four groups of mice; the negative control group (Ctrl), which received $^{175}$Lu-DTPA-PLO-microspheres; and three treated groups, which received $^{177}$Lu-DTPA-PLO-microspheres with radioactivities of 0.82, 1.1, and 1.37 MBq. For each of the three treatment groups, 0.82, 1.1, and 1.37 MBq, there was a statistically significant reduction in tumour growth between days 5 and 11, as measured by the decreased change in bioluminescence flux produced by the luciferase-transfected tumour cells (p=0.011, 0.026, and 0.0017, respectively). The negative control group had a median change in bioluminescence 1.9, 1.8, and 2.3 times larger than the treated groups, 0.82, 1.1, and 1.37 MBq, respectively.

Example 16: The Effect of Internal Radiation from $^{177}$Lu-DTPA-PLO-Microspheres on the Growth of Mouse B16-F10-Luc2 Tumours in Mouse Lungs The lungs are identified as the most frequent site of distant melanoma metastases with very poor patient outcome (Tas, F., & Erturk, K. (2017). Recurrence behavior in early-stage cutaneous melanoma: pattern, timing, survival, and influencing factors. Melanoma Research, 27(2), 134-139. http://doi.org/10.1097/CMR.0000000000000332). The C57BL/6 derived B16 melanoma is a commonly used mouse lung metastasis model. The effect of internal radiation from $^{177}$Lu-DTPA-PLO-microspheres on the growth of the B16-F10-luc2 cell line, transfected with luciferase, in the lungs of BALB/c mice was investigated.

Tumours were grown in the lungs of 18 BALB/c mice by injecting B16-F0-luc2 cells (100 000 cells) intravenously (via a tail vein). At 7 days of tumour growth the lung bioluminescence was measured with an IVIS Spectrum in vivo imaging system (PerkinElmer) and the mice were divided into two groups; a treatment group (n=10), and a negative control group (n=10) bearing approximately equal total tumour burdens. The mice in the treatment group were then injected intravenously (via a tail vein) with a preparation of $^{177}$Lu-DTPA-PLO-microspheres (3 mg/kg), such that each mouse received an average activity of 1.60 MBq. Mice in the negative control group were injected with a non-radioactive $^{175}$Lu-DTPA-PLO-microsphere preparation (3 mg/kg). The microspheres were 8 µm diameter and were injected as a suspension in saline (0.17 mL). At 12 days of growth (after 5 days of exposure to internal radiation), the tumour bioluminescence was measured and the difference in bioluminescence between the two measurements was calculated for individual mice. These results are shown in FIG. 11.

Figure 11:
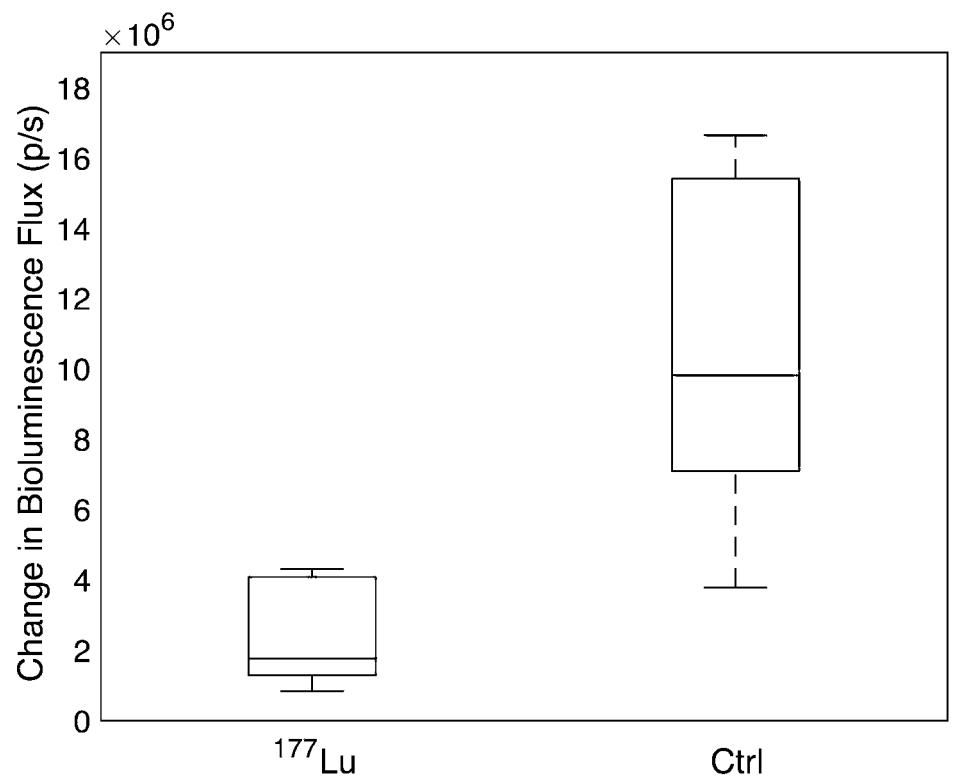
FIG. 11 shows the effect of the internal ionizing radiation from $^{177}$Lu-DTPA-PLO-microspheres on the growth of mouse lung B 6-F10-luc2 tumours. The results are shown for two groups of mice; the treated group ($^{177}$Lu), which received $^{177}$Lu-DTPA-PLO-microspheres; and the negative control group (Ctrl), which received $^{175}$Lu-DTPA-PLO-microspheres.

Shown in FIG. 11 is the effect of the internal ionizing radiation from $^{177}$Lu-DTPA-PLO-microspheres on the growth of mouse lung B16-F10-luc2 tumours. The results are shown for two groups of mice; the treated group ($^{177}$Lu), which received $^{177}$Lu-DTPA-PLO-microspheres; and the negative control group (Ctrl), which received $^{175}$Lu-DTPA-PLO-microspheres. The treated mice showed a statistically significant reduction in tumour growth (p=0.0004) between days 7 and 12, as measured by the decreased change in bioluminescence flux produced by the luciferase-transfected tumour cells. The negative control group had a median change in bioluminescence 5.56 times larger than the treated group.

Example 17: Histology of Lungs from Normal Mice Exposed to Intravenously Injected $^{177}$Lu-DTPA-PLO-Microspheres for 24 Days This study tested the effect of the internal radiation treatment on normal mouse lungs without tumours, to provide some evidence of tolerance. Five BALB/c mice were injected intravenously (via a tail vein) with either a preparation of $^{177}$Lu-DTPA-PLO-microspheres (3 mice) or $^{175}$Lu-DTPA-PLO-microspheres (2 mice). The microspheres were 8 µm diameter and were injected as a suspension in 5% dextrose solution (0.17 mL) at a loading of 3 mg/kg. The mice that received $^{177}$Lu received an average activity of 1.66 MBq. The welfare of the mice was carefully monitored every day and the mice were scored (0-3) against several standard mouse model criteria, as above for mice with tumours. Twenty-four days following injection, the mice were euthanised and the lungs were removed and fixed in 10% neutral buffered formalin. A single lung from each mouse was sent to an accredited veterinary pathology laboratory for histology and reporting by a qualified pathologist, who was unaware of which mice had received internal radiation treatment and which had received control treatment.

Figure 12:
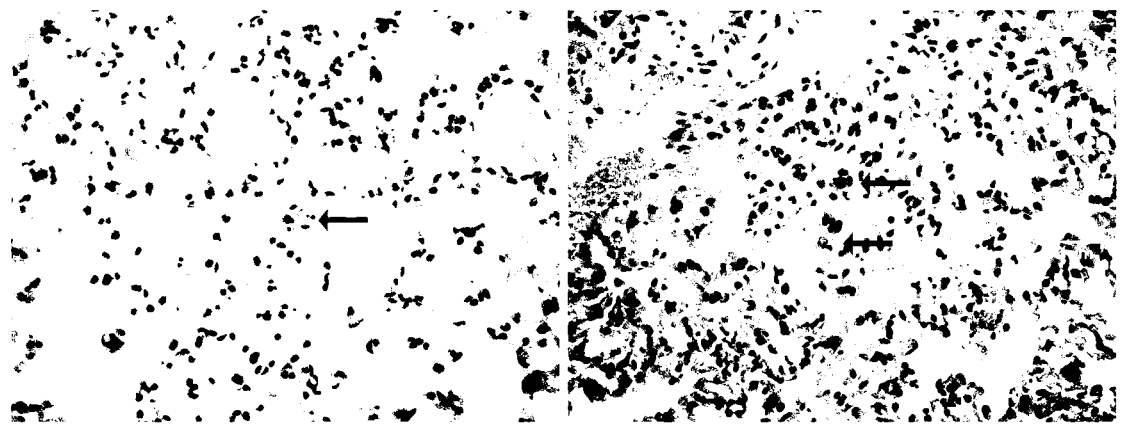
FIG. 12 shows the histology of lungs from normal mice exposed to intravenously injected $^{177}$Lu-DTPA-PLO-microspheres for 24 days.

The results obtained from this study showed firstly that there was negligible impact of the internal radiation therapy on the welfare of the normal mice over the 24 days of careful daily monitoring. The general behavior and condition of the treated and control mice were indistinguishable. Secondly, regarding histological findings, FIG. 12 shows lung tissue from the mice stained with hematoxylin and eosin at 40× magnification. Some of the microspheres are highlighted with arrows and the white bars show 50 µm. The pathologist's report stated, "There were large numbers of microspheres that were widely and randomly scattered throughout the lung. Overall, lung samples from each of the 5 mice were essentially the same. There was no significant histological evidence of inflammation associated with the microspheres. Also there was no evidence of fibrosis in the lung. Furthermore there was no evidence of fibrin deposition and no evidence of pulmonary megakaryocytes (platelets). There did not appear to be any adverse effects on the lung tissue, of mice in this study, due to radiation exposure."

Example 18: Histology of Mouse Lungs with 4T1-Luc2 Tumours Exposed to Intravenously Injected $^{177}$Lu-DTPA-PLO-Microspheres for 5 Days Tumours were grown in the lungs of 20 BALB/c mice by injecting 4T1-luc2 cells (50000 cells) intravenously (via a tail vein). At 5 days of tumour growth the lung bioluminescence was measured with an IVIS Spectrum in vivo imaging system (PerkinElmer) and the mice were divided into two groups; a treatment group (n=9), and a negative control group (n=9) bearing approximately equal total tumour burdens. The mice in the treatment group were then injected intravenously (via a tail vein) with a preparation of $^{177}$Lu-DTPA-PLO-microspheres (3 mg/kg), such that each mouse received an average activity of 1.6 MBq. Mice in the negative control group were injected with a non-radioactive $^{175}$Lu-DTPA-PLO-microsphere preparation (3 mg/kg). The microspheres were 8 µm diameter and were injected as a suspension in 5% dextrose solution (0.17 mL). At 10 days of growth (after 5 days of exposure to internal radiation), the mice were culled and the lungs were removed for histological analysis. Four lungs from each group were sent to an accredited veterinary pathology laboratory for histology and reporting by a qualified pathologist, who was unaware of which mice had received internal radiation treatment and which had received control treatment.

Figure 13:
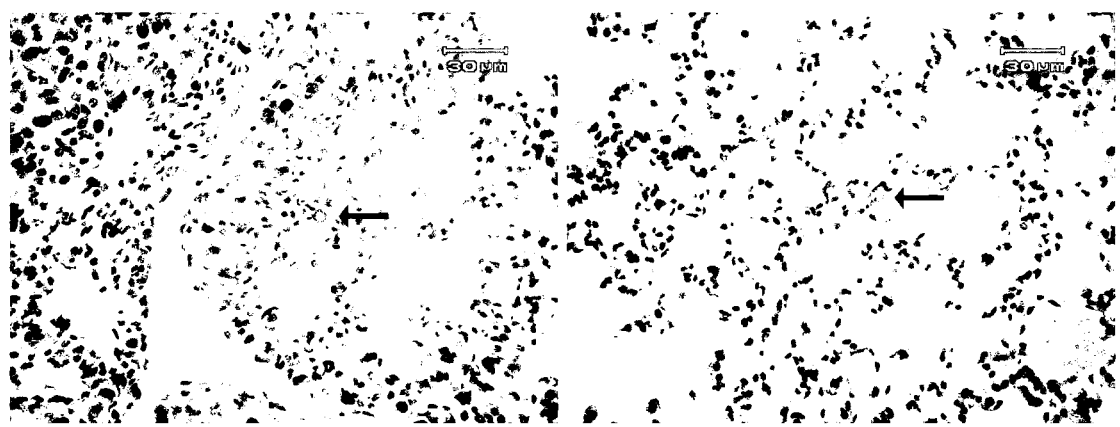
FIG. 13 shows the histology of mouse lungs with 4T1-luc2 tumours exposed to intravenously injected $^{177}$Lu-DTPA-PLO-microspheres for 5 days.

Firstly, over the course of the experiment the mice were carefully monitored and there was no impact on their welfare from the internal radiation therapy. Secondly, regarding histological findings, FIG. 13 shows lung tissue from the mice stained with hematoxylin and eosin at 40× magnification. Some of the microspheres are highlighted with arrows. The pathologist's report stated, "Microspheres were widely and randomly distributed throughout the lung. As a general rule more were in both the interstitial tissue of the lung than within tumours. I found the results from the different mice reasonably consistent, and really no discernible difference between any of the mice. There was very little inflammation around the microsphere and mostly no inflammation around the microspheres. There was either no inflammation around microspheres. Or in some mice, a very mild neutrophilic infiltrate around a small number of microspheres. All mice had microspheres within tumours. Microspheres can also be found adjacent to tumours. There was cell death and necrosis in all tumours, regardless of whether they had microspheres in them or not. I looked for generalized inflammation of the lung, to assess the potential for radiation damage to the lung. I did not think there was significant generalized inflammation of the lung tissue and therefore I did not think there was obvious radiation to the lung. There was no evidence of pulmonary syncytial cells and no evidence of fibrosis in the lung. There was inflammation in the tumours and essentially the same mild degree of inflammation whether there were microspheres in the tumour or not. There was degeneration and necrosis of tumour cells. I reviewed these cases without knowledge of which mice were treated and which mice were controls. However, all mice were essentially the same and there did not seem to be a significant difference between mice."

Example 19: The Short-Term Effect of Intravenously Injected $^{177}$Lu-DTPA-PLO-Microspheres on Full Blood Counts of Mice Over 5 Days The BALB/c mouse strain may not be the most appropriate model to investigate the biological effects of the internal radiation on the lungs. The CBA mouse strain has been suggested as a better model to investigate radiation pneumonitis and pulmonary fibrosis (Dabjan, M. B. et al., 2016. A survey of changing trends in modelling radiation lung injury in mice: Bringing out the good, the bad, and the uncertain. Laboratory Investigation, 96(9), pp. 936-949.)

Figure 14:
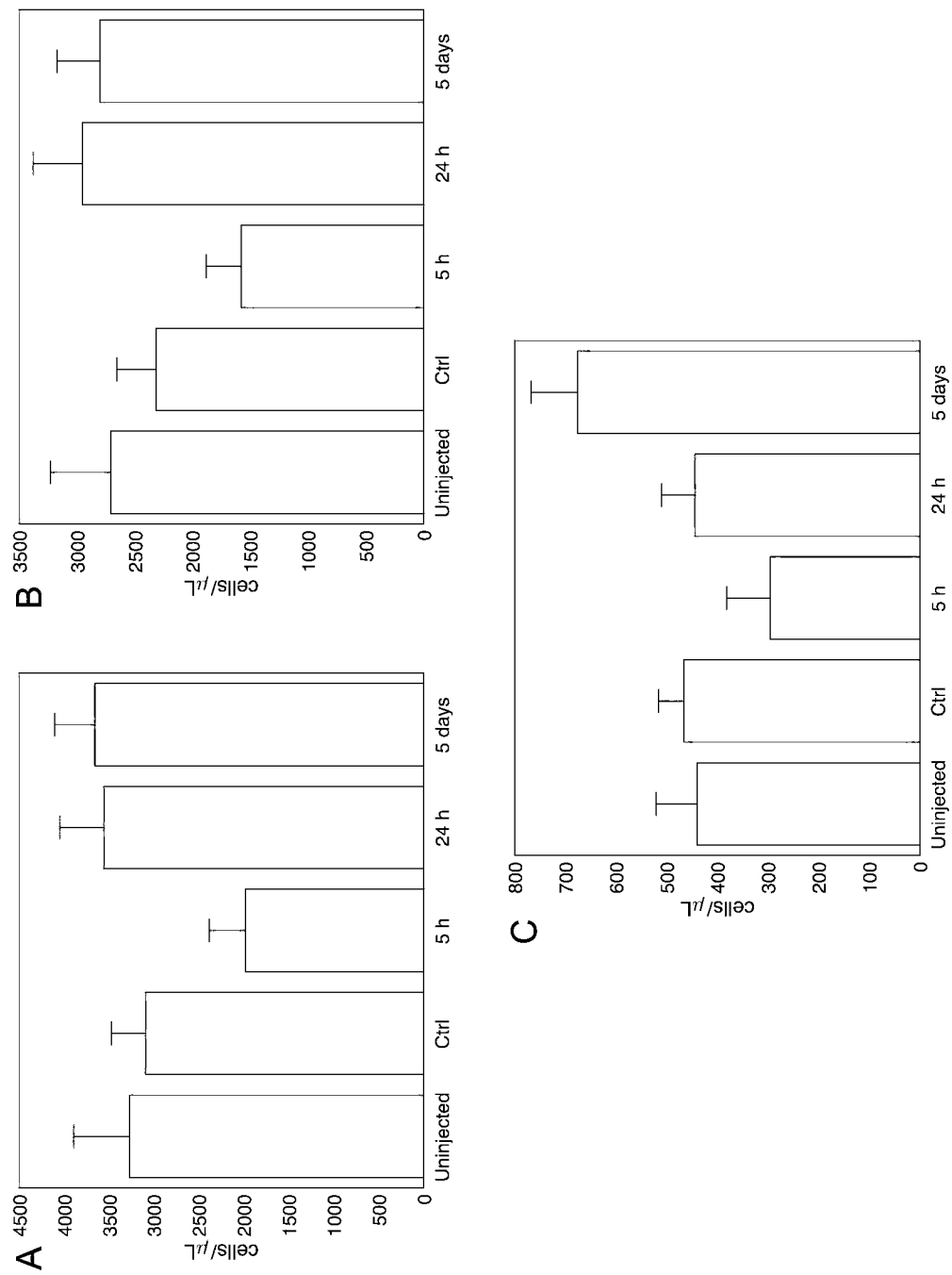
FIG. 14 shows the effect of intravenously injected $^{177}$Lu-DTPA-PLO-microspheres on full blood counts of mice over 5 days. The effect of the internal radiation on the full white blood cell counts, lymphocyte cell counts and neutrophil cell counts are shown in FIGS. 14A, B and C respectively.

This study tested the short-term effect of the internal radiation treatment on full blood cell counts to provide further evidence of tolerance. Five groups of 5 CBA mice were injected intravenously (via a tail vein) with either a preparation of $^{177}$Lu-DTPA-PLO-microspheres (3×5 mice), or $^{175}$Lu-DTPA-PLO-microspheres (5 mice). The remaining 5 mice were left as an un-injected control to investigate the effects of the intravenous microsphere injections. The microspheres were 8 µm diameter and were injected as a suspension in saline (0.17 mL) at a loading of 3 mg/kg. The mice that received $^{177}$Lu received an average activity of 1.6 MBq. The welfare of the mice was carefully monitored every day and the mice were scored (0-3) against several standard mouse model criteria. At 5 hours, 24 hours and 5 days post-injection, the three treatment group mice were anaesthetized and blood was collected by cardiac puncture into a syringe preloaded with anticoagulant. At 5 hours, post-injection, the negative control mice were anaesthetized and blood was collected by cardiac puncture into a syringe preloaded with anticoagulant. Blood was also collected from the un-injected control group of mice by the same procedure. The collected bloods were analysed on a Advia 2120 hematology system (Siemens), and results are shown in FIG. 14.

The effect of the internal radiation treatment on the full white blood cell counts, lymphocyte cell counts, and neutrophil cell counts are shown in FIGS. 14A, B, and C, respectively. A slight drop in cell counts were seen after 5 hours exposure to the internal radiation; However, this was not statistically significant and the cell levels had recovered by 24 hours. After 5 days exposure, a slightly elevated level of neutrophils was measured, though again this was not statistically significant. No other changes were observed in the full red blood cell counts and parameters such as the measured hemoglobin, mean corpuscular volume, and hematocrit.

Bloods collected from control and treated groups of mice were also processed to isolate peripheral blood mononuclear cells (PBMCs) and used to assess DNA damage. PBMCs were isolated by Ficoll-Paque density gradient centrifugation, adhered to microscope slides and stained with γH2AX and 53BP1 antibodies to indicate the presence of double stranded DNA breaks, referred to as foci. PBMCs were imaged using confocal microscopy (Leica SPI, Leica Microsystems) and DNA damage foci were quantified using Fiji Imaging Software. Foci analysis aimed to quantify a minimum of 100 PBMCs for γH2AX and 53BP1 markers.

Figure 15:
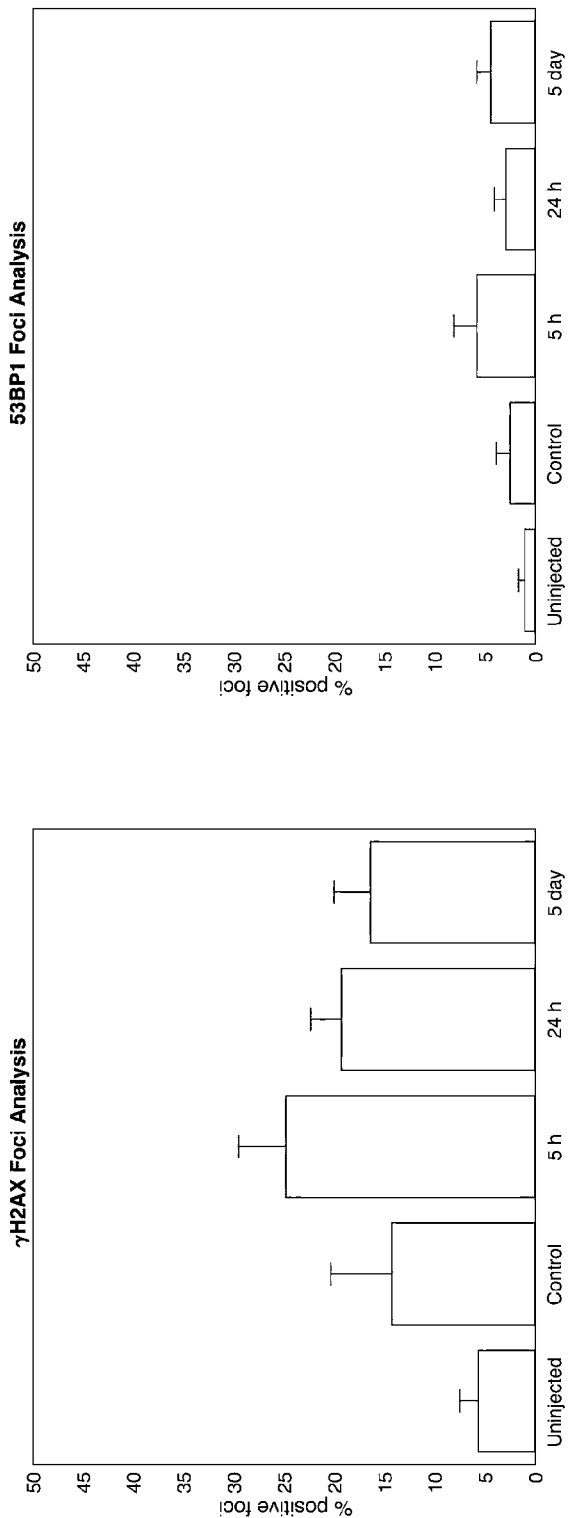
FIG. 15 shows the results from the analysis of DNA damage of peripheral blood mononuclear cells (PBMC) from intravenously injected $^{177}$Lu-DTPA-PLO-microspheres over 5 days. Isolated PBMCs were imaged using confocal microscopy and DNA damage foci were identified with γH2AX (left) and 53BP1 (right) antibodies.

Results from the analysis of PBMCs' DNA damage response to internal radiation treatment are shown in FIG. 15. An increased percentage of PBMCs with γH2AX and 53BP1 foci were observed in the treated group 5 hours post-injection. However, this increase was not statistically significant when compared with the negative control group and returned to a similar level as the negative control group at 5 days post-injection. Negative control mice injected with $^{175}$Lu-DTPA-PLO-microspheres showed an increased percentage of foci compared to un-injected mice, however, this increase is not statistically significant.

Figure 16:
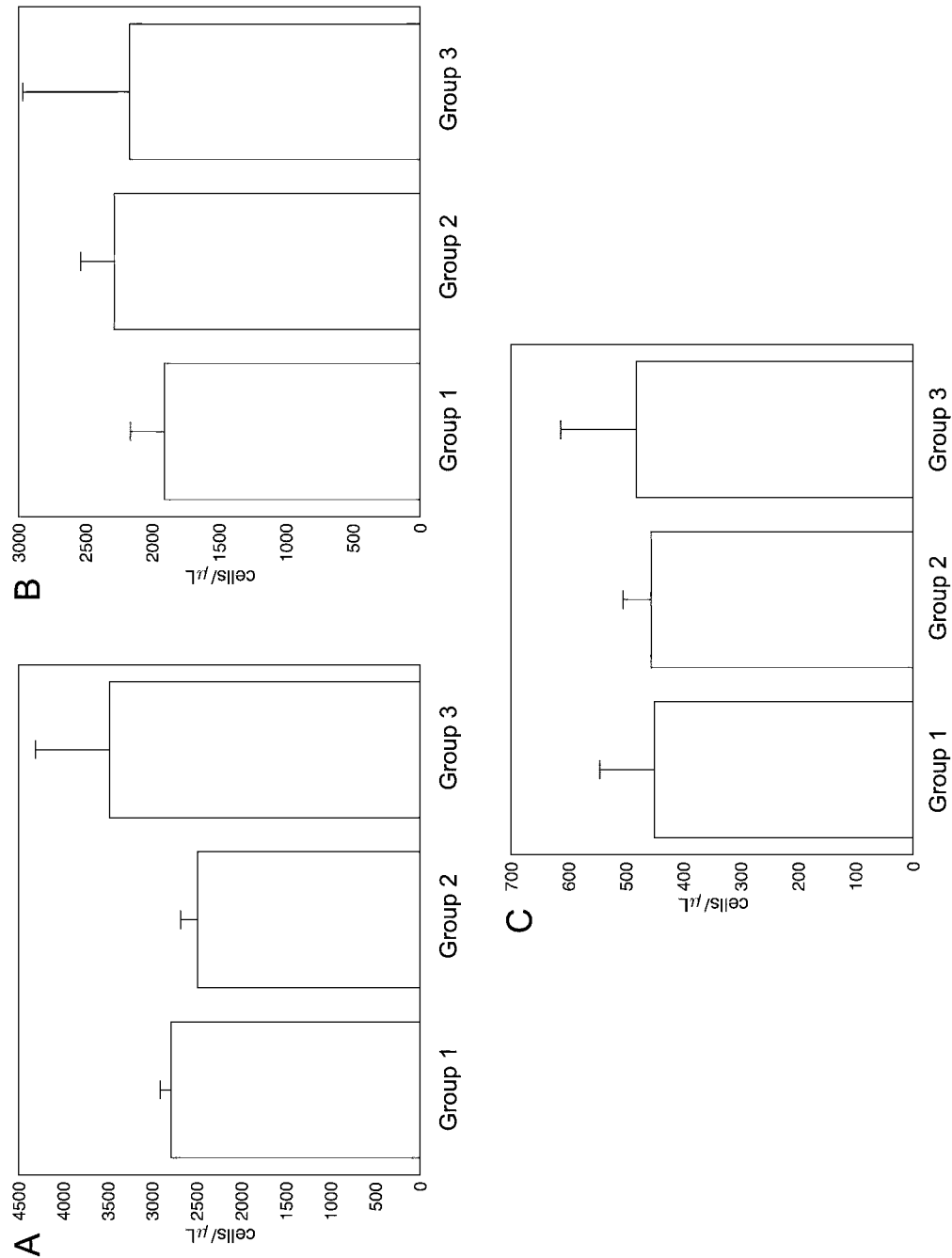
FIG. 16 shows the effect of intravenously injected $^{177}$Lu-DTPA-PLO-microspheres on full blood counts of mice after 3 months. The effect of the internal radiation on the full white blood cell counts, lymphocyte cell counts and neutrophil cell counts are shown in FIGS. 16A, B and C respectively.

Example 20: The Long-Term Effect of Intravenously Injected $^{177}$Lu-DTPA-PLO-Microspheres on Full Blood Counts of Mice Over 3 Months This study assessed the long-term effect of the lung internal radiation treatment on full blood cell counts to provide further evidence of tolerance of the $^{177}$Lu-DTPA-PLO-microspheres. Three groups of CBA mice were injected intravenously (via a tail vein) with either a preparation of $^{175}$Lu-DTPA-PLO-microspheres (group 1, 3 mice, non-radioactive control), $^{177}$Lu-DTPA-PLO-microspheres at 0.55 MBq (group 2, 5 mice) or $^{177}$Lu-DTPA-PLO-microspheres at 1.1 MBq (group 3, 5 mice). The microspheres were 8 μm diameter and were injected as a suspension in saline (0.17 mL) at a loading of 3 mg/kg. The mice that received $^{177}$Lu, received an average activity of 0.51 and 1.0 MBq for groups 2 and 3, respectively. Estimated average lung absorbed doses were calculated based on past retention data to be 23.2 and 46.1 Gy for groups 2 and 3, respectively. The welfare of the mice was carefully monitored daily for 14 days, followed by welfare assessments twice a week. The mice were scored (0-3) against several standard mouse model criteria. At 3 months post-injection, the mice were anaesthetized and blood was collected by cardiac puncture into a syringe preloaded with anticoagulant (0.18% EDTA in PBS). The collected blood samples were analysed on an Advia 2120 hematology system (Siemens), and the results are shown in FIG. 16.

The effect of the internal radiation treatment on the total white blood cell counts, lymphocyte cell counts, and neutrophil cell counts are shown in FIGS. 16A, B and C, respectively. Mice in group 3 exhibited a slightly elevated white blood cell count, however, this was not statistically significant. Lymphocyte and neutrophil counts between control and $^{177}$Lu injected groups revealed no significant changes. No changes were observed in the red blood cell counts, or in other parameters such as the measured hemoglobin, mean corpuscular volume, and hematocrit.

Bloods collected from control and treated groups of mice were also processed to isolate peripheral blood mononuclear cells (PBMCs) and used to assess DNA damage. PBMCs were isolated by Ficoll-Paque density gradient centrifugation, adhered to microscope slides and stained with γH2AX and 53BP1 antibodies to indicate the presence of double stranded DNA breaks, referred to as foci. PBMCs were imaged using confocal microscopy (Leica SPI, Leica Microsystems) and DNA damage foci were quantified using Fiji Imaging Software. Foci analysis aimed to quantify a minimum of 100 PBMCs for γH2AX and 53BP1 markers.

Figure 17:
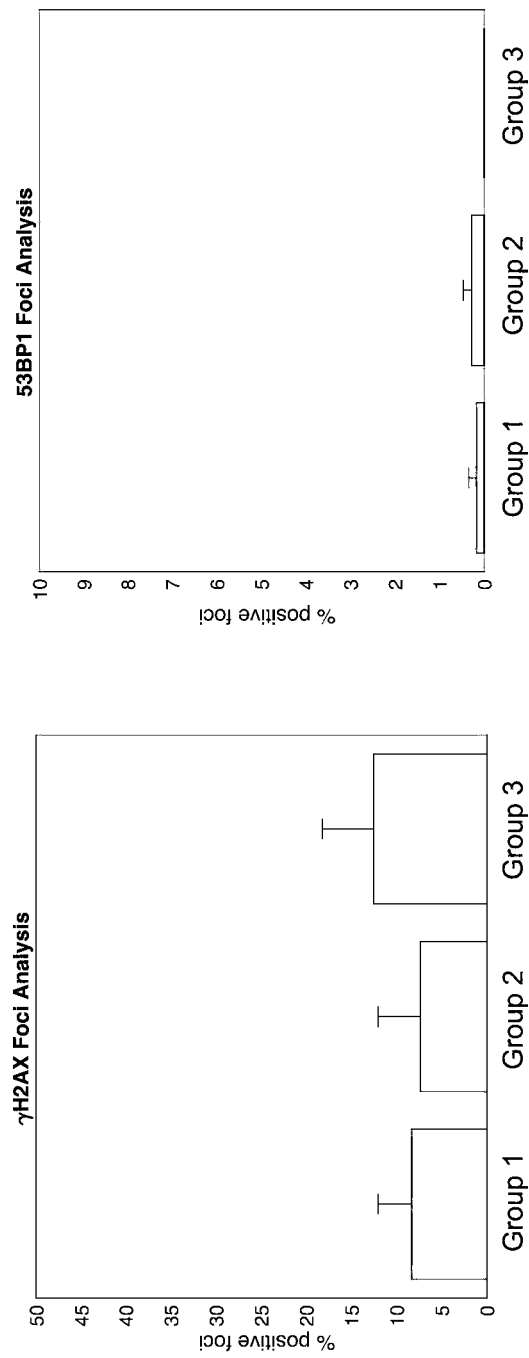
FIG. 17 shows the results from the analysis of DNA damage of peripheral blood mononuclear cells (PBMC) from intravenously injected $^{177}$Lu-DTPA-PLO-microspheres after 3 months. Isolated PBMCs were imaged using confocal microscopy and DNA damage foci were identified with γH2AX (left) and 53BP1 (right) antibodies.

Results from the analysis of PBMCs' DNA damage response to internal radiation treatment are shown in FIG. 17. No significant differences were observed in the percentage of γH2AX and 53BP1 foci between control and 177Lu injected groups.

Example 21: Histology of Mouse Lungs Exposed to Intravenously Injected $^{177}$Lu-DTPA-PLO-Microspheres for 3 Months Three groups of CBA mice were injected intravenously (via a tail vein) with either a preparation of $^{175}$Lu-DTPA-PLO-microspheres (group 1, 3 mice, non-radioactive control), $^{177}$Lu-DTPA-PLO-microspheres at 0.55 MBq (group 2, 5 mice) or $^{177}$Lu-DTPA-PLO-microspheres at 1.1 MBq (group 3, 5 mice) as described in Example 20. The welfare of the mice was carefully monitored daily for 14 days, followed by welfare assessments twice a week. The mice were scored (0-3) against several standard mouse model criteria. At 3 months post-injection, and following blood collection (Example 20), the mice were euthanised by cervical dislocation and the lungs and heart were collected. Samples of lung and heart tissue from each mouse was sent to an accredited veterinary pathology laboratory for histology and reporting by a qualified pathologist, who was unaware of which mice had received internal radiation treatment and which had received control treatment.

The results obtained from this study showed firstly that there was negligible impact of the internal radiation therapy on the welfare of the normal mice over the 24 days of careful daily monitoring. The general behavior and condition of the treated and control mice were indistinguishable. Secondly, regarding histological findings, the pathologist's report stated, "The mice examined were 31, 41, 51, 23, 24, 45, 15, 42, 44. All of the lungs contained microspheres. The heart, and pericardium were also examined. Other adjacent tissues including the oesophagus, trachea, skeletal muscle and bronchial lymph node were also examined. There was a mild increase in the number of alveolar macrophages in the all of the lungs of all mice. I think this is due to pulmonary oedema and may be an incidental finding associated with euthanasia. In the lungs, in and around the microspheres, there was no evidence of inflammation, fibrin deposits, platelet syncytia, necrosis or fibrosis. There was no evidence of any inflammation or necrosis or other tissue reaction, associated with radiation exposure, in the heart or pericardium. Also there was no evidence of any inflammation or necrosis in the other associated tissues such as oesophagus, trachea, skeletal muscle or bronchial lymph node." A summary of the pathologist's report can be seen in Table 7.

TABLE 7

| Group | Mouse ID | Fibrosis | Cell Death | Platelet Syncytia | Fibrin Deposits | Inflammation-Lymphocytes and Neutrophils | Mild Increased Alveolar Macrophages |
|---|---|---|---|---|---|---|---|
| 1 | 31 | mild reaction | No | No | No | No | Yes |
| 1 | 41 | No | No | No | No | No | Yes |
| 1 | 51 | No | No | No | No | No | Yes |
| 2 | 23 | No | No | No | No | No | Yes |
| 2 | 24 | No | No | No | No | No | Yes |
| 2 | 45 | No | No | No | No | No | Yes |
| 3 | 15 | No | No | No | No | No | Yes |
| 3 | 42 | No | No | No | No | No | Yes |
| 3 | 44 | No | mild reaction | No | No | No | Yes |

Figure 18:
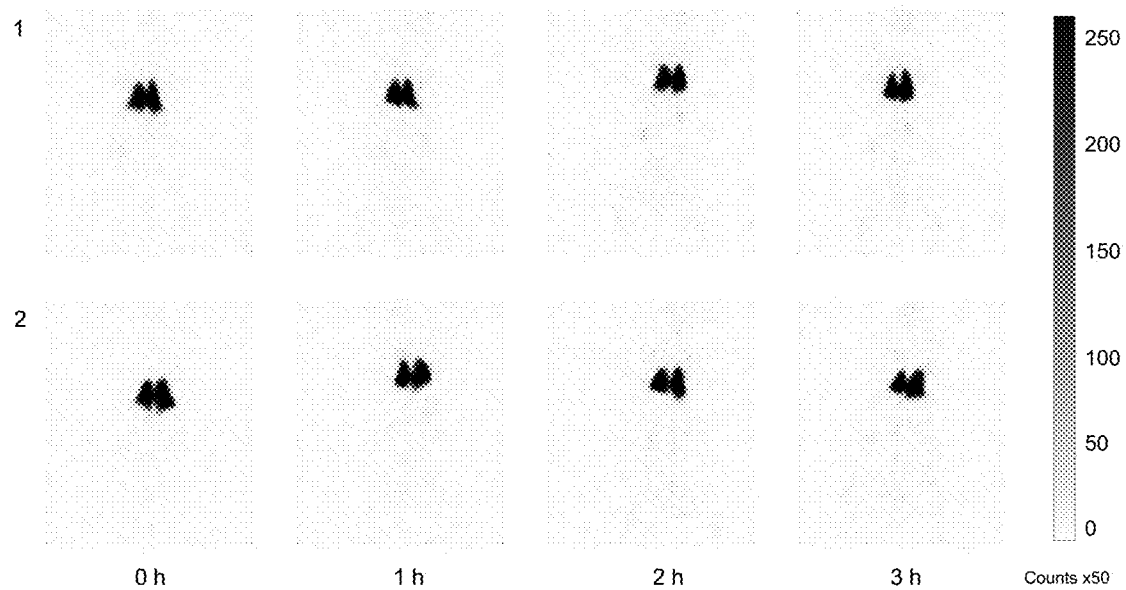
FIG. 18 shows the gamma camera images of two rabbits injected intravenously (via an ear vein), under anaesthesia, with $^{177}$Lu-DTPA-PLO-microspheres (3.9 mg/kg). The microspheres were 8 µm diameter and were injected in a 5% dextrose solution. Gamma camera images were obtained immediately following injection, as well as at 1, 2, and 3 hours post-injection, while under anaesthesia. The counts of the images were multiplied by a factor of 50 for visualisation.

Example 22: Stability Test of $^{177}$Lu-DTPA-PLO-Microspheres In Vivo Short-Term Rabbit Lung Retention Test The previous tests all referred to mouse models, and it was desirable to validate the biodistribution and stability results in a different animal species, preferably non-rodent. Rabbits were selected due to a) their larger size enabling better imaging of biodistribution in the relevant organs, and b) enabling administration of microspheres via a different route of intravenous injection, i.e. through an ear vein. Two New Zealand white rabbits were injected intravenously (via an ear vein), under anaesthesia, with $^{177}$Lu-DTPA-PLO-microspheres (3.9 mg/kg). The microspheres were 8 μm diameter and were injected in a 5% dextrose solution (3 mL), such that each rabbit received an average activity of 107 MBq. Gamma camera images of the rabbits were obtained immediately following injection, as well as at 1, 2, and 3 hours post-injection, while under anaesthesia (FIG. 18). The counts of the images were multiplied by a factor of 50 for visualization. Additionally, 2 New Zealand white rabbits were injected intravenously (via an ear vein), under anaesthesia, with the $^{177}$Lu-DTPA-PLO polymer (with no microspheres) and 2 rabbits with free $^{177}$LuCl$_3$, in 5% dextrose solutions with average radioactivities of 120 and 112 MBq, respectively.

The $^{177}$Lu-DTPA-PLO-microspheres were lodged at limiting diameters of the pulmonary circulation where the gamma-emitting isotope persisted. FIG. 18 depicts the efficient retention of radiolabel on microspheres trapped in the vascular network of the lungs. After 3 hours, the animals were culled and lungs and liver were dissected. Separate gamma camera images of the organs and the carcass revealed that 95.7±0.3% of the total radioactivity was found retained in the lungs, 0.2±0.02% in the liver, and 4.1±0.2% in the carcass (Table 8). In contrast, free $^{177}$LuCl$_3$ was not retained in the lungs and rapidly associated with bones of the carcass. The polymer $^{177}$Lu-DTPA-PLO, not bound to microspheres, also was not retained in lungs, however large levels of radioactivity was found in the kidneys and bladder of the rabbits, 11.5 and 63.3%, respectively. This indicates that the polymer bound form of $^{177}$Lu is rapidly eliminated via the renal system.

Figure 19:
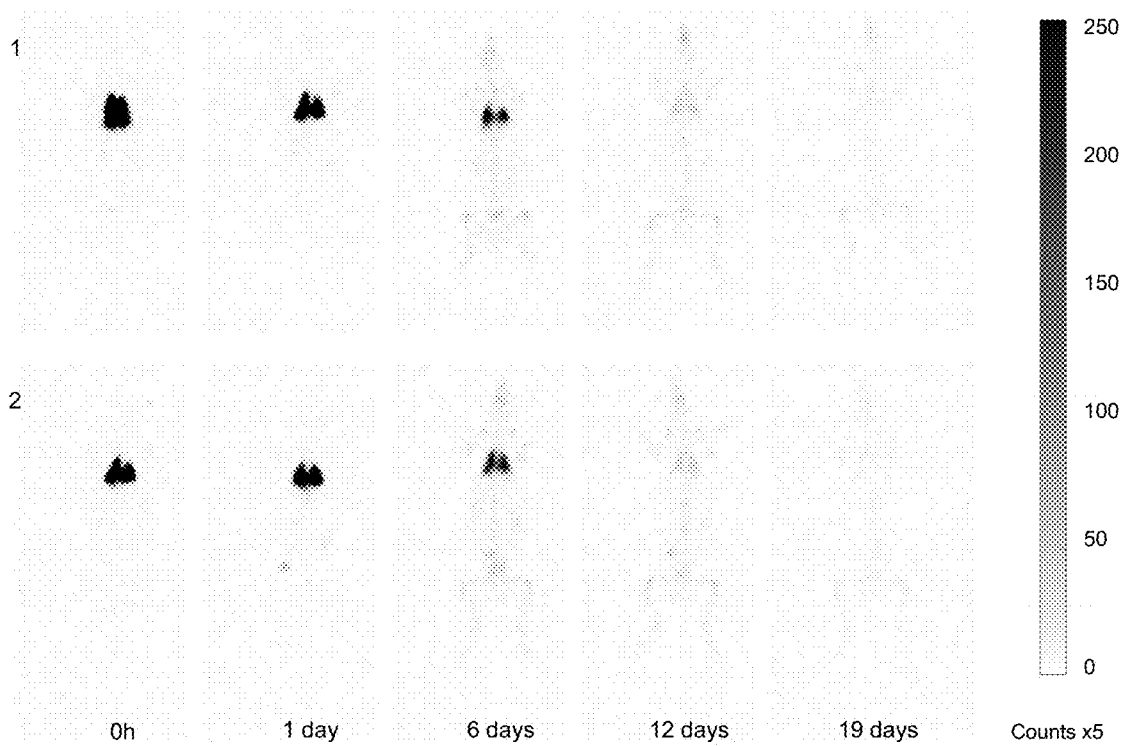
FIG. 19 shows the gamma camera images of two rabbits injected intravenously (via an ear vein), under anaesthesia, with $^{177}$Lu-DTPA-PLO-microspheres (3 mg/kg). The microspheres were 8 µm diameter and were injected in saline. Gamma camera images were obtained immediately following injection, as well as at 1, 6, 12 and 19 days post-injection, on each occasion under anaesthesia. The counts of the images were multiplied by a factor of 5 for visualization.

Example 23: Stability Test of $^{177}$Lu-DTPA-PLO-Microspheres In Vivo—Long-Term Rabbit Lung Retention Test Two New Zealand white rabbits were injected intravenously (via an ear vein), under anesthesia, with $^{177}$Lu-DTPA-PLO-microspheres (3 mg/kg). The microspheres were 8 m diameter and were injected in saline (3 mL), such that each rabbit received an average activity of 74.9 MBq. Gamma camera images of the rabbits were obtained immediately following injection, as well as at 1, 6, 12 and 19 days post-injection, on each occasion under anesthesia (FIG. 19). The counts of the images were multiplied by a factor of 5 for visualization. The general behavior and condition of the rabbits was closely monitored daily post-injection to assess any impact on welfare. From the rabbit gamma camera images in FIG. 19, gamma counts of individual organs were obtained by drawing regions of interest on the images. These were converted to actual activities through a single point calibration with a known source. These data are summarised in Table 9.

As with the mouse experiments above, intravenous injection and persistence of radioactive microspheres in the lungs of rabbits was well tolerated over 19 days; there was no discernible impact on welfare. Gamma camera imaging of the rabbits during administration demonstrated that the radiolabelled microspheres injected via the ear vein route quantitatively transited the venous return to the heart, also the right-side heart chambers and then were subsequently retained in the lungs (FIG. 19). It is clear that a significant amount of activity is retained in the lungs after 6 days, an average of 40.9% of the activity that was injected (corrected for decay), which is comparable to the retention of the radioactive microspheres in the lungs of mice (44.6%, Table 5).

TABLE 8

| Agent | Lungs % Total | Liver % Total | Spleens % Total | Carcass Total | Kidney % Total | Bladder % Total |
|---|---|---|---|---|---|---|
| $^{177}$Lu-DTPA-PLO-MS | 95.93 | 0.20 | — | 3.86 | ND | ND |
| $^{177}$Lu-DTPA-PLO-MS | 95.41 | 0.24 | 0.01 | 4.30 | ND | ND |
| Mean ± SEM | 95.67 ± 0.26 | 0.22 ± 0.02 | 0.01 | 4.08 ± 0.22 | — | — |
| $^{177}$LuCl$_3$ | 5.73 | 4.40 | 0.04 | 90.00 | ND | ND |
| $^{177}$LuCl$_3$ | 1.39 | 3.41 | 0.07 | 95.13 | ND | ND |
| Mean ± SEM | 3.31 ± 1.92 | 3.91 ± 0.50 | 0.05 ± 0.01 | 92.57 ± 2.57 | — | — |
| $^{177}$Lu-DTPA-PLO | 1.05 | 3.67 | 0.04 | 29.45 | 17.35 | 47.88 |
| $^{177}$Lu-DTPA-PLO | 0.53 | 2.54 | 0.00 | 17.87 | 5.59 | 78.75 |
| Mean ± SEM | 0.79 ± 0.26 | 3.10 ± 0.56 | 0.02 ± 0.02 | 23.66 ± 5.79 | 11.47 ± 5.88 | 63.32 ± 15.44 |

TABLE 9

| Rabbit # | Time | Lung Activity MBq | Lung Retention % Injected | Lung Counts | Lung % Total | Kidney Counts | Kidney % Total | Skeleton Counts | Skeleton % Counts | Total Counts |
|---|---|---|---|---|---|---|---|---|---|---|
| 1 | 0 h | 71.12 | 93.41 | 88028 | 93.84 | 172 | 0.18 | 5606 | 5.98 | 93806 |
| 2 | 0 h | 69.16 | 93.82 | 85464 | 94.18 | 139 | 0.15 | 5142 | 5.67 | 90745 |
| 1 | 1 day | 62.41 | 90.98 | 77249 | 94.49 | 80 | 0.10 | 4426 | 5.41 | 81755 |
| 2 | 1 day | 61.78 | 93.02 | 76345 | 94.24 | 117 | 0.14 | 4553 | 5.62 | 81015 |
| 1 | 6 days | 16.48 | 40.47 | 20399 | 60.38 | 1024 | 3.03 | 12364 | 36.59 | 33787 |
| 2 | 6 days | 16.27 | 41.25 | 20099 | 56.95 | 2094 | 5.93 | 13102 | 37.12 | 35295 |
| 1 | 12 days | 2.16 | 9.93 | 2677 | 22.92 | 741 | 6.35 | 8260 | 70.73 | 11678 |
| 2 | 12 days | 2.05 | 9.70 | 7579 | 20.65 | 803 | 6.56 | 8917 | 72.80 | 12249 |
| 1 | 19 days | 0.39 | 3.67 | 477 | 13.44 | 554 | 15.61 | 2517 | 70.94 | 3548 |
| 2 | 19 days | 0.41 | 4.00 | 503 | 12.50 | 479 | 11.90 | 3042 | 75.60 | 4024 |

Figure 20:
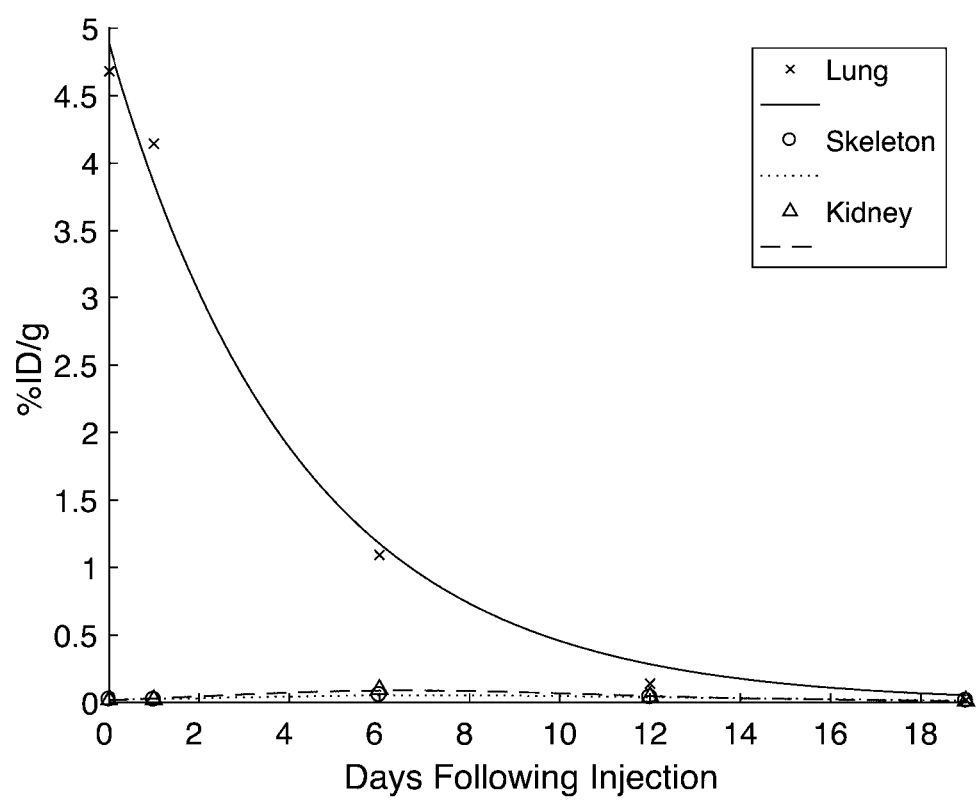
FIG. 20 shows the percent injected dose (% ID) per gram wet weight of tissue that was delivered to the rabbit lungs, skeleton and kidney over a 19 day time course following intravenous injection of $^{177}$Lu-DPTA-PLO microspheres.

Example 24: The Absorbed Doses Delivered to Rabbit Organs Exposed to Intravenously Injected $^{177}$Lu-DTPA-PLO-Microspheres The gamma counts and activities for New Zealand white rabbit lungs, skeleton and kidney, shown in Table 9, were used to calculate the percent injected dose per gram wet weight of tissue that was delivered to those organs over the 19 day time course (FIG. 20). This was calculated assuming an average tissue wet weight of 20 g for the rabbit lungs, 15 g for the kidneys and a weight of 265.2 g for the rabbit skeleton (6% of the average rabbit weight; Stephen W Barthold, 2015. Pathology of Laboratory Rodents and Rabbits, Fourth Edition). As with the mice, the rabbit lungs receive the majority of the dose per gram of tissue over time. Radiation Absorbed Doses were estimated using the Medical Internal Radiation Dose (MIRD) schema and ignoring the small contribution due to the gamma emissions from $^{177}$Lu. The absorbed dose received by the lung injected with an activity of 74.9 MBq on the $^{177}$Lu-DTPA-PLO-microspheres over 19 days, was estimated to be 31.1 Gray, while the absorbed dose to the kidneys and skeleton was estimated to be only 1.5 and 1.1 Gray, respectively.

Figure 21:
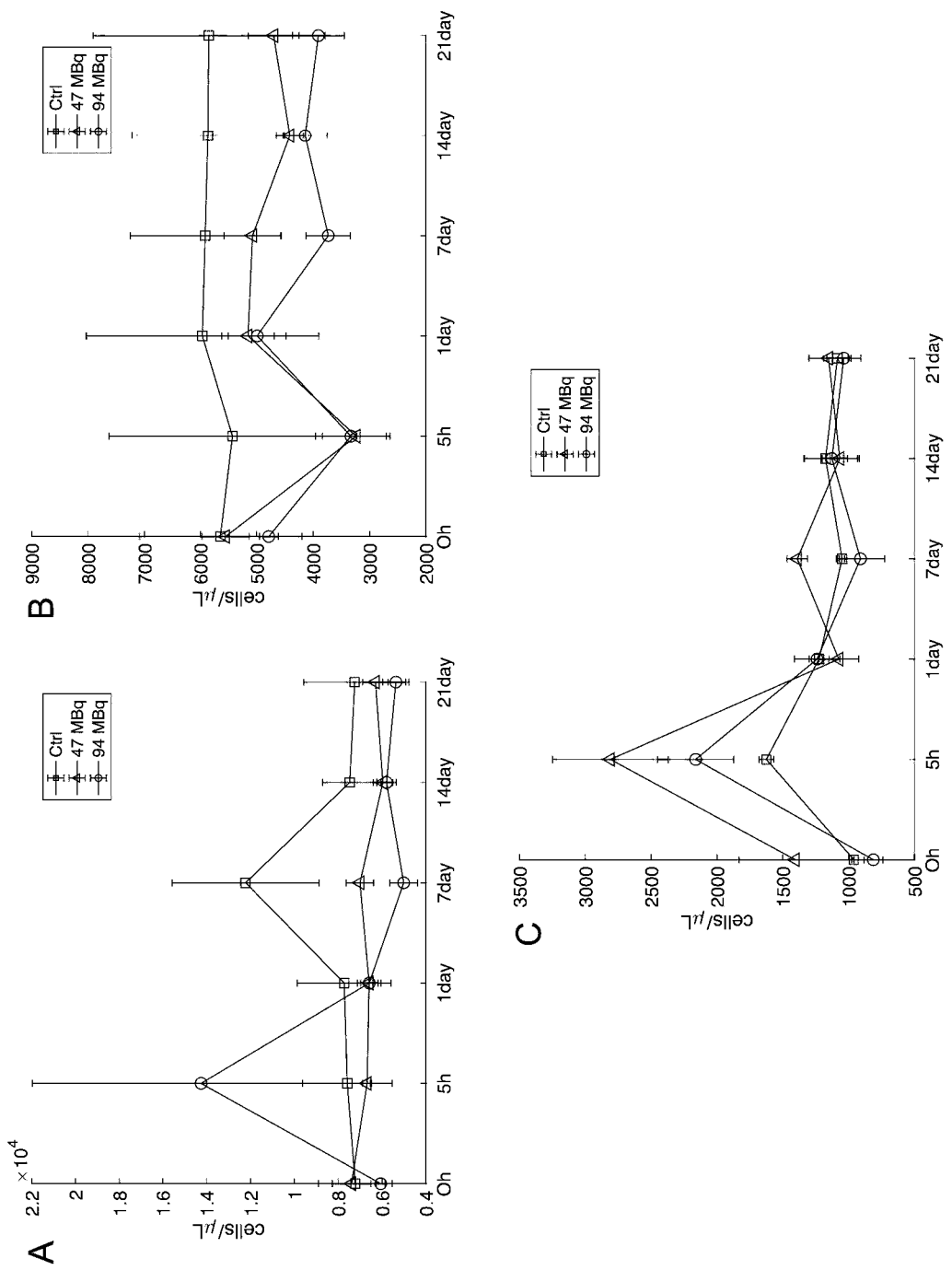
FIG. 21 shows the effect of intravenously injected $^{177}$Lu-DTPA-PLO-microspheres on full blood counts of rabbits over time. The effect of the internal radiation on the full white blood cell counts, lymphocyte cell counts and neutrophil cell counts are shown in FIGS. 21A, B and C respectively.

Example 25: The Effect of Intravenously Injected $^{177}$Lu-DTPA-PLO-Microspheres on Fill Blood Counts of Rabbits Over Time This study tested the effect of the internal radiation treatment on full blood cell counts to provide further evidence of tolerance. Ten New Zealand white rabbits were injected intravenously (via an ear vein), under anesthesia, with either $^{177}$Lu-DTPA-PLO-microspheres (2 mg/kg; 2×4 rabbits), or $^{175}$Lu-DTPA-PLO-microspheres (2 mg/kg; 2 rabbits) as a negative control. The microspheres were 8 μm diameter and were injected in saline (3 mL), and the rabbits injected with $^{177}$Lu received an average activity of either 47, or 94 MBq. The general behavior and condition of the rabbits was closely monitored daily post-injection to assess any impact on welfare. Immediately prior to injection and at 5 hours, 24 hours, 7 days, 14 days and 21 days post-injection, blood was collected via an ear vein into a syringe preloaded with anticoagulant. The collected bloods were analysed on a Advia 2120 hematology system (Siemens), and results are shown in FIG. 21.

The effect of the internal radiation treatment on the full white blood cell counts, lymphocyte cell counts, and neutrophil cell counts are shown in FIGS. 21A, B, and C, respectively. At 5 hours exposure to the internal radiation treatment there was an increase in the mean total white blood cell counts for the highest activity group, 94 MBq, though this was highly variable within the same group (n=4). A decrease in lymphocytes, and an increase in neutrophils was also measured for both of the treatment groups, and these cell counts returned to normal levels by 24 hours. No other changes were observed in the full red blood cell counts and parameters such as the measured hemoglobin, mean corpuscular volume, and hematocrit.

Example 26: Histology of Rabbit Lungs Exposed to Intravenously Injected $^{177}$Lu-DTPA-PLO-Microspheres for 3 Months Three groups of New Zealand white rabbits were injected intravenously (via an ear vein), under anesthesia, with either $^{175}$Lu-DTPA-PLO-microspheres (group 1, 1 rabbit) or $^{177}$Lu-DTPA-PLO-microspheres (groups 2 and 3, 2 rabbits each), at a loading of 3 mg/kg. The microspheres were 8 μm diameter and were injected in saline (3 mL), and groups 2 and 3 received an average radioactivity of 39 and 90 MBq, respectively. The general behavior and condition of the rabbits was closely monitored daily post-injection to assess any impact on welfare. At 3 months post-injection, the rabbits were culled and the heart and lungs were collected. Tissue samples from the lungs, heart and pericardium were sent to an accredited veterinary pathology laboratory for histology and reporting by a qualified pathologist, who was unaware of which rabbit had received internal radiation treatment and which had received the control treatment.

Figure 22:
FIG. 22 shows the histology of rabbit lungs exposed to intravenously injected $^{177}$Lu-DTPA-PLO-microspheres for 3 months.

Firstly, over the course of the experiment the rabbits were carefully monitored and there was no impact on their welfare from the internal radiation therapy. Secondly, regarding histological findings, FIG. 22 shows lung tissue from the rabbits stained with hematoxylin and eosin at 40× magnification. A single rabbit from group 2 presented with a moderate inflammatory response that was often associated with the microspheres (FIG. 22, left). However, this was not present in the other rabbit of group 2, nor in the group 3 rabbits that received a higher dose of radioactivity.

The pathologist's report stated, "Rabbit 254, had multiple small well delineated granulomas randomly dispersed throughout the pulmonary parenchyma. These granulomas often contained a microsphere at their centre. The granulomas were formed by aggregates of macrophages and lymphocytes, but there was no significant evidence of necrosis or fibrin deposition. Rabbits 260, 263, 274, 272 had no significant lung lesions, although there were large numbers of microspheres widely dispersed throughout the lung. That is there was no fibrosis, cell death, platelet syncytia, fibrin deposits or inflammation or pulmonary histiocytosis. There were no histological lesions in the pericardium or the heart of rabbits 254, 260, 263, 274, 272. More specifically there was no fibrosis, cell death, platelet syncytia, fibrin deposits or inflammation. There was no histological difference in the side of the heart that was in contact with the lung and the side of the heart that was not in contact with the lung." A summary of the report is shown in Table 10.

TABLE 10

| Group | ID | Lung Inflammation | Heart Inflammation | Pericardium Inflammation | Type of inflammation |
|---|---|---|---|---|---|
| 1 | 272 | No | No | No | No inflammation |
| 2 | 254 | Moderate reaction | No | No | Multifocal granulomas lungs |
| 2 | 260 | No | No | No | No inflammation |
| 3 | 263 | No | No | No | No inflammation |
| 3 | 274 | No | No | No | No inflammation |

Example 27: Stability Test of $^{177}$Lu-DTPA-PLO-Microspheres In Vivo—Short-Term Rabbit Liver Retention Test This test was performed as an indicator of labeled microsphere stability in the environment of a different internal organ, i.e. in the liver as opposed to all results above done where the microspheres were retained in the lungs. This has relevance to any potential clinical use of the internal radiation therapy of the invention in treating liver tumours. Five New Zealand white rabbits were anaesthetised with isoflurane, intubated, given fluids (Hartmann's solution) intravenously, and placed on a heated airbed for the surgical procedure. The hepatic artery was exposed via mid-line laparotomy (open surgery) and catheterised by microsurgery for the instillation of either $^{177}$Lu-DTPA-PLO-microspheres (3 rabbits) or $^{177}$LuCl$_3$ (2 rabbits). The microspheres were 8 µm diameter and were injected in 5 mL of a 5% dextrose solution at an average loading of 13 mg/kg, with an average radioactivity of 109 MBq. The $^{177}$LuCl$_3$ was injected in 5 mL of a 5% dextrose solution with an average activity of 105 MBq. Normal blood flow to the liver was re-established and the rabbits were imaged with an Infinia Hawkeye 4 SPECT scanner (GE Healthcare). One hour after surgery and imaging, the rabbits were euthanised by lethal intracardiac injection with sodium pentobarbitone while still under anaesthesia, and the organs removed for further SPECT imaging. The organ counts are shown in Table 11.

These results confirmed an even higher rate of short-term retention of microspheres in the rabbit liver compared to the rabbit lungs (99.7% versus 95.7% respectively), which clearly satisfies an important requirement for application of the labeled microspheres in internal radiation therapy of liver tumours. By contrast, soluble $^{177}$Lu was rapidly depleted from the liver and distributed systemically into the carcass.

Example 28: Stability Test of $^{177}$Lu-DTPA-PLO-Microspheres In Vivo—Short-Term Rabbit Liver VX2 Tumour Retention Test Liver VX2 tumours were grafted onto one of the major liver lobes of New Zealand white rabbits using keyhole surgery to implant two approximately 1 mm$^3$ cubes of tumour tissue into a small incision. All surgery on liver graft recipients was performed using sterile field preparation, with autoclaved instruments and the rabbits were anaesthetised with isoflurane. After 3 weeks of tumour growth, 9 rabbits were anaesthetised with isoflurane, intubated, given fluids (Hartmann's solution) intravenously, and placed on a heated airbed for the surgical procedure. The hepatic artery was exposed via mid-line laparotomy (open surgery) and catheterised by microsurgery for the instillation of either $^{177}$Lu-DTPA-PLO-microspheres (7 rabbits) or $^{177}$LuCl$_3$ (2 rabbits). The microspheres were 8 µm diameter and were injected in 5 mL of a 5% dextrose solution at an average loading of 12 mg/kg, with an average radioactivity of 112 MBq. The $^{177}$LuCl$_3$ was injected in 5 mL of a 5% dextrose solution with an average activity of 82 MBq. Normal blood flow to the liver was re-established and the rabbits were imaged with an Infinia Hawkeye 4 SPECT scanner (GE Healthcare). One hour after surgery and imaging, the rabbits were euthanised by lethal intracardiac injection with sodium pentobarbitone while still under anaesthesia, and the organs removed for further SPECT imaging. The organ counts are shown in Table 12.

Figure 23:
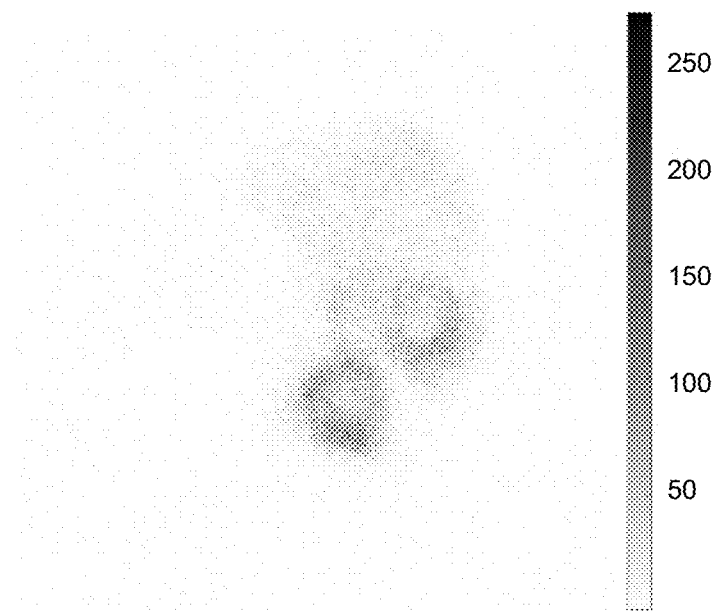
FIG. 23 shows a gamma camera image of an excised rabbit liver with two VX2 tumours following instillation of $^{177}$Lu-DTPA-PLO-microspheres.

Gamma camera imaging of the excised liver (FIG. 23) showed circular halos of enhanced radioactivity in the peripheral growth zones of two implanted tumours, presumably in the angiogenic plexus induced by the tumours. Soluble $^{177}$Lu administered intra-arterially was rapidly lost from the liver as above for normal livers and did not provide useful imaging of tumours.

TABLE 11

| Agent | Liver % Total | Lungs % Total | Blood % Total | Carcass % Total |
|---|---|---|---|---|
| $^{177}$Lu-DTPA-PLO-MS | 99.9 | 0.08 | 0.19 | 0.02 |
| $^{177}$Lu-DTPA-PLO-MS | 99.9 | 0.06 | ND | ND |
| $^{177}$Lu-DTPA-PLO-MS | 99.3 | 0.54 | ND | 0.2 |
| Mean ± SEM | 99.7 ± 0.2 | 0.2 ± 0.16 | 0.06 ± 0.06 | 0.073 ± 0.064 |
| $^{177}$LuCl$_3$ | 20 | 1.3 | 15.7 | 78.2 |
| $^{177}$LuCl$_3$ | 3.82 | 5.4 | 12.1 | 90.4 |
| Mean ± SEM | 11.9 ± 8.1 | 3.4 ± 2.1 | 13.9 ± 1.8 | 84.3 ± 6.1 |

TABLE 12

| Agent | No. VX2 Implants | Excised Liver % Total | Tumour Lobe % Total | Tumour Vol. mm³ | Excised Lungs % Total | Blood % Total | Carcass % Total |
|---|---|---|---|---|---|---|---|
| $^{177}$Lu-DTPA-PLO-MS | | | | | | | |
| 1 | 2 | 98.9 | 54.7 | 144 | 0.54 | ND | 0.55 |
| 1 | 2 | 96.4 | 47.9 | 6237 | 1.13 | 0.7 | 2.45 |
| 3 | 1 | 99.3 | 10 | 0.68 | 0.68 | ND | ND |
| 4 | 1 | 98.6 | 18.3 | 0.32 | 0.32 | 0.19 | 0.97 |
| 5 | 1 | 99.7 | 36 | 0.11 | 0.11 | 0.04 | 0.09 |
| 6 | 1 | 99.1 | 47.2 | 0.92 | 0.92 | 0.07 | ND |
| 7 | 1 | 98.9 | 44 | 1.04 | 1.04 | 0.03 | ND |
| Mean ± SEM | | 98.7 ± 0.4 | 36.9 ± 6.3 | 0.68 ± 0.14 | 0.68 ± 0.14 | 0.15 ± 0.10 | 0.58 ± 0.34 |
| $^{177}$LuCl$_3$ | | | | | | | |
| 1 | 1 | 27.9 | 10 | 1.1 | 1.1 | 9.6 | 70.7 |
| 2 | 1 | 30.3 | 3.7 | 1.2 | 1.1 | 10.2 | 68.2 |
| Mean ± SEM | | 29.1 ± 1.2 | 6.9 ± 3.2 | 1.15 ± 0.05 | 1.15 ± 0.05 | 9.9 ± 0.3 | 69.5 ± 1.3 |

Example 29: Stability Test of $^{177}$Lu-DTPA-PLO-Microspheres In Vivo—Long-Term Subcutaneous Mouse 4T1-Luc2 Tumour Retention Test This study was done to inform on utility in treating subcutaneous tumours, as distinct from the above examples with lung and liver tumours. Polymer microspheres (1 µm diameter) were radiolabelled with $^{177}$LU using DTPA-PLO as the immobilizing agent. A suspension of microspheres (16.7 mg/mL; 245 MBq/mL; 18 µL) was injected directly into subcutaneously grown mouse 4T1-luc2 tumours at day 8 of growth. The tumours were grown from the subcutaneous injection of 2 000 000 4T1-luc2 cells in 30 µL of Hank's balanced salt solution. After 4 more days of tumour growth the mice were dissected and the distribution of radioactivity was determined in the tumour, liver and carcass by gamma camera imaging with an Infinia Hawkeye 4 SPECT scanner (GE Healthcare). The results are shown in Table 13. The excised tumours were found to contain a high proportion of total radioactivity (mean 97.4%) at day 12, i.e. 4 days post-injection of isotope.

Figure 24:
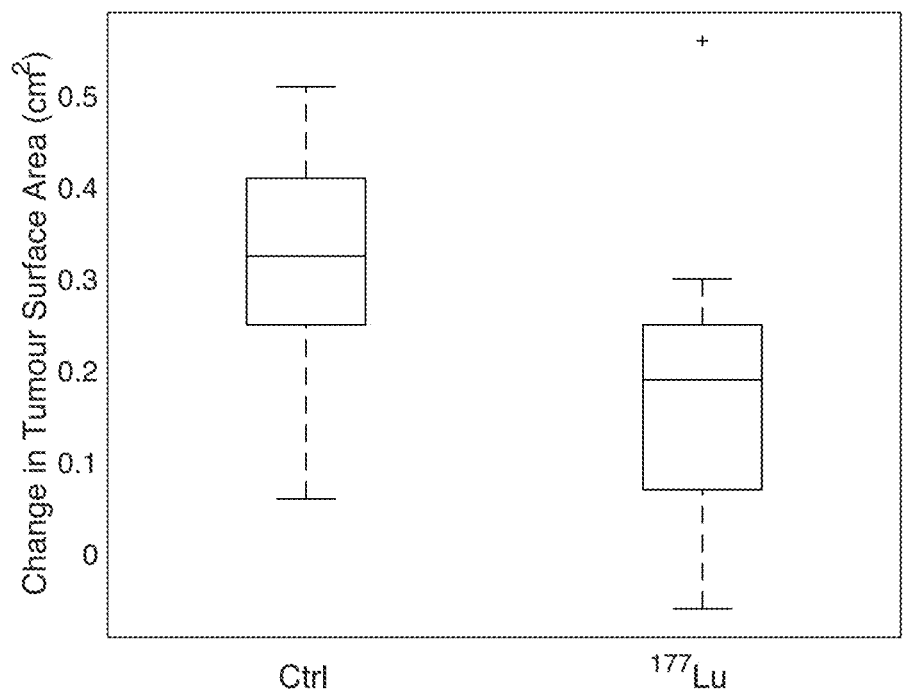
FIG. 24 shows the effect of $^{177}$Lu-DTPA-PLO-microspheres (1 µm; 15 mg/kg) on the growth of subcutaneous mouse tumours after direct intra-tumoural injection and exposure for 4 days. Tumours were grown for 8 days prior to injection, and the change in tumour surface area was measured as the change in bioluminescence area from 4T1-luc2 cells, following intraperitoneal injection of luciferin, between days 8 and 12 of tumour growth. The control group received the same size and quantity of non-radioactive $^{175}$Lu-DTPA-PLO-microspheres.

Example 30: The Effect of $^{177}$Lu-DTPA-PLO-Microspheres on Subcutaneous Mouse 4T-Luc2 Tumour Growth Shown in FIG. 24 is the effect of $^{177}$Lu radiolabelled microspheres on the growth of mouse 4T1-luc2 subcutaneous tumours, measured in the anaesthetised mice using an IVIS Spectrum in vivo imaging system (PerkinElmer), which measured the tumour bioluminescence emission after injection (IP) of luciferin. The results are shown for two groups of mice with tumours; the untreated group (Ctrl; n=10) were injected intra-tumorally with non-radioactive $^{175}$Lu-DTPA-PLO-microspheres at day 8 and the treated group ($^{177}$Lu; n=9) were injected intra-tumorally with $^{177}$Lu-DTPA-PLO-microspheres at day 8. The microspheres were 1 µm diameter and were injected in 18 µL of a 5% dextrose solution at a loading of 0.3 mg, with an average radioactivity of 4.4 MBq. Each tumour was used as its own control and the growth increment was calculated by subtracting the area of bioluminescence emission imaged in the tumour at day 8 from the area imaged at day 12. Mouse subcutaneous tumours that were treated with the $^{177}$Lu-DTPA-PLO-microspheres were 59% smaller in size (p=0.058).

The invention claimed is:

1. A radiolabelled material comprising:
   (i) a polymer;
   (ii) a radioactive isotope; and
   (iii) an immobilizing agent;
   wherein the polymer is a cationic exchange resin comprising anionic substituent groups; and
   wherein the immobilizing agent is capable of immobilizing the radioactive isotope on or in the polymer, and
   wherein the immobilizing agent is a macromolecule comprising a polycation with multiple pendant metal-chelating agent side-chains.

2. The radiolabelled material according to claim 1, wherein the polycation has a polypeptide backbone with pendant side chains covalently attached at intervals of 2 to 6 amino acid residues apart.

3. The radiolabelled material according to any preceding claim, wherein the metal-chelating agent is selected from the

TABLE 13

| Mouse# | Tumour Volume [mm3] | Tumour Counts | Tumour % Total | Liver Counts | Liver % Total | Carcass Counts | Carcass % Total | Total Counts |
|---|---|---|---|---|---|---|---|---|
| 1 | 73 | 4009 | 100 | — | — | — | — | 4009 |
| 2 | 148 | 4490 | 100 | — | — | — | — | 4490 |
| 3 | 113 | 3985 | 100 | — | — | — | — | 3985 |
| 4 | 101 | 2602 | 79.6 | 185 | 5.7 | 482 | 14.7 | 3269 |
| 5 | 136 | 3479 | 99.4 | — | — | 20 | 0.6 | 3499 |
| 6 | 163 | 3640 | 98.3 | — | — | 63 | 1.7 | 3703 |
| 7 | 122 | 3007 | 99.6 | — | — | 12 | 0.4 | 3019 |
| 8 | 143 | 5374 | 100 | — | — | — | — | 5374 |
| 9 | 149 | 2854 | 100 | — | — | — | — | 2854 |
| Mean | 128 | 3715 | 97.4 | 20.5 | 0.6 | 64.1 | 1.9 | 3800 | group consisting of ethylene diamine tetraacetic acid (EDTA), 1,4,7,10-tetraazacyclododecane-1,4,7,10-N,N',N",N'"-tetraacetic acid (DOTA), diethylene triamine pentaacetic acid (DTPA), mercaptoacetyltriglycine (MAG$_3$), 6-Hydrazinopridine-3-carboxylic acid (Hynic), dimercaptosuccinic acid (DMSA), ethylene glycol-bis(β-aminoethyl ether)-N,N,N',N'-tetraacetic acid (EGTA), triethylenetramine (TETA), 1,4,7,10-tetraazacyclotridecane-1,4,7,10-N,N',N",N'"-tetraacetic acid (TRITA), 1,4,7-triazacyclononane-1,4,7-triacetic acid (NOTA), deferoxamine (desferral), sarcophagine (SarAr), 1,4,7,10-tetraazacyclododecane-1,4,7,10-N,N',N",N'"-tetra(methylene) phosphonic acid (DOTMP); 1,4,7,10-tetraazacyclotridecane-1,4,7,10-N,N',N",N'"-tetra(methylene)phosphonic acid; 1,4,7,10-tetraazacyclotetradecane-1,4,7,10-N,N',N",N'"-tetra(methylene) phosphonic acid; diethylene triamine-N,N',N"-pentaacetic acid and isomeric derivatives thereof; cryptate [2,2,2], cryptate[3,2,2], cryptate[2,2,1] and mono and di-benzo derivatives thereof; bridged calix[4]arenes containing electron rich (donor) groups (hydroxyl, carboxyl, ester, amid, amine); 1,10-diaza-4,7,13,16-tetraoxacyclooctadecane-1,10-N,N'-bis-acetic acid; and 1,10-diaza-4,7,13, 16 tetraoxacyclooctadecane-1,10-N,N'-bis-malonate.

4. The radiolabelled material of claim 1, wherein the metal chelating agent is selected from DOTA and DTPA.

5. The radiolabelled material of claim 1, wherein the metal chelating agent is selected to maintain immobilization of the selected radioisotope(s) under in vivo conditions.

6. The radiolabelled material of claim 1, wherein the macromolecule is poly-D-lysine (PDL) or poly-L-ornithine (PLO).

7. The radiolabelled material of claim 1, wherein the one or more radioactive isotopes are capable of imaging, therapy, or both.

8. The radiolabelled material of claim 1, wherein the one or more radioactive isotope is selected from the group consisting of Ac-225, Au-198, Bi-212, Bi-213, Co-57, Cr-51, Cu-64, Cu-67, Dy-165, Er-169, Fe-59, Ga-67, Ga-68, Gd-153, Ho-166, In-111, Ir-192, Lu-177, Pd-103, Rb-81, Rb-86, Re-186, Re-188, Ru-103, Sc-47, Sm-153, Sn-117m, Sr-89, Tb-161, Tc-99m, Tl-201, Y-90, Yb-169 and Zr-89.

9. The radiolabelled material of claim 1 comprising a combination of at least two radioactive isotopes capable of imaging, therapy, or both.

10. The radiolabelled material of claiml, further comprising at least one non-radioactive carrier metal.

11. The radiolabelled material of claim 1, wherein at least one of the radioactive isotopes emits gamma, beta, or positron radiation, or a combination thereof.

12. A method of radiation therapy of a patient, the method comprising administering to said patient a therapeutically effective amount of the radiolabelled material of claim 1.

13. A method for the treatment of cancer, the method comprising administering a therapeutically effective amount of the radiolabelled material of claim 1.

14. The method of claim 13, wherein the radiolabelled material is administered by intravenous injection.

15. A medical device comprising the radiolabelled material of claim 1.

16. A method of imaging a medical procedure in a patient, the method comprising administering to said patient the radiolabelled material of claim 1, and detecting said radiolabelled material in said patient.

17. The radiolabelled material of claim 1, wherein the polymer is polystyrene sulfonate.

18. The radiolabelled material of claim 1, wherein the particulate microspheres have a median diameter of 8 microns.

19. The radiolabelled material of claim 1, wherein the radioactive isotope is Lu-77.

* * * * *

UNITED STATES PATENT AND TRADEMARK OFFICE
CERTIFICATE OF CORRECTION

PATENT NO. : 11,896,683 B2
APPLICATION NO. : 16/469244
DATED : February 13, 2024
INVENTOR(S) : Ross Wentworth Stephens et al.

It is certified that error appears in the above-identified patent and that said Letters Patent is hereby corrected as shown below:

In the Claims

Column 42, in Claim 1, Line 38 "a radioactive isotope" should read – one or more radioactive isotopes –.

Column 42, in Claim 1, Lines 40-59 "wherein the polymer is a cation exchange resin comprising sulfonate substituent groups; and
wherein the immobilizing agent is capable of immobilizing the radioactive isotope on or in the polymer," should read – wherein the polymer is a cation exchange resin comprising sulfonate substituent groups; and wherein the polymer comprises particulate microspheres having a median diameter in the range from about 8 to about 12 microns; and
wherein the immobilizing agent is capable of immobilizing the one or more radioactive isotopes on or in the polymer, –.

Column 42, in Claim 3, Line 66 "The radiolabelled material according to any preceding claim" should read – The radiolabelled material of claim 1 –.

Column 43, in Claim 5, Lines 24-26 "The radiolabelled material of claim 1, wherein the metal chelating agent is selected to maintain immobilization of selected radioisotope(s) under in vivo conditions." should read – The radiolabeled material of claim 1, wherein the metal chelating agent is capable of maintaining immobilization of the one or more radioactive isotopes under in vivo conditions. –.

Column 44, in Claim 10, Line 8 "The radiolabelled material of claim1," should read – The radiolabelled material of claim 1 –.

Signed and Sealed this
Fourteenth Day of May, 2024

Katherine Kelly Vidal
*Director of the United States Patent and Trademark Office*